United States Patent [19]

Daneshvar

[11] Patent Number: 5,514,155
[45] Date of Patent: May 7, 1996

[54] DEVICE FOR APPLYING PRESSURE TO A PERSON'S GROIN

[76] Inventor: Yousef Daneshvar, 21459 Woodfarm, Northville, Mich. 48167

[21] Appl. No.: 165,835

[22] Filed: Dec. 14, 1993

[51] Int. Cl.⁶ ................................................. A61B 17/12
[52] U.S. Cl. .............................. 606/201; 602/53; 602/62; 128/118.1
[58] Field of Search ........................... 606/112, 201–204; 128/118.1, 96.1, 98.1; 602/13, 53, 55, 67, 62, 47, 58, 59, 61

[56] References Cited

U.S. PATENT DOCUMENTS

| | | | |
|---|---|---|---|
| 2,054,768 | 9/1936 | Gale | 602/59 |
| 2,493,406 | 1/1950 | Hicks | 128/118.1 X |
| 3,171,410 | 3/1965 | Towle et al. | 128/118.1 X |
| 4,135,503 | 1/1979 | Romano | 128/118.1 X |
| 4,436,089 | 3/1984 | Schmid | 602/53 |
| 4,622,957 | 11/1986 | Curlee | 128/118.1 |
| 4,917,112 | 4/1990 | Kalt | 602/58 |
| 4,957,105 | 9/1990 | Kurth | 128/96.1 |
| 4,977,893 | 12/1990 | Hunt | 128/96.1 X |
| 5,170,781 | 12/1992 | Loomis | 128/118.1 |

FOREIGN PATENT DOCUMENTS

| | | | |
|---|---|---|---|
| 910340 | 6/1946 | France | 128/118.1 |
| 821824 | 11/1951 | Germany | 128/118.1 |
| 45062 | 7/1908 | Switzerland | 128/118.1 |
| 4383 | of 1880 | United Kingdom | 128/118.1 |
| 9011744 | 10/1990 | WIPO | 606/202 |

Primary Examiner—Michael H. Thaler

[57] ABSTRACT

This application introduces an improved and modified version of previously applied means of prevention from bleeding by this applicant. The previous applications were as follows D. Device, Pressure bandages and dressings, Device 2, D. Device 3, and D. Device 4 which were all primarily designed for this purpose. Here again wraps are primarily made from a non-stretchable material although elastic materials are introduced in which these wraps will allow the application of pressure by an inflatable balloon, fluid-filled bag, or even a hard proper plate to certain wounds on the body to prevent bleeding and related complications. In this application it is stressed that the front part of these units on the wound will be made clear to allow visualization of the wound. A hard plastic is also introduced to be placed in front of the balloon or on the wound site. Many other modifications are introduced as well. The inventor believes that these units will be very useful in this regard. The unit with only minimal modification can also be very useful in patients with inguinal hernia, after hernia operations, or similar surgeries as well.

16 Claims, 21 Drawing Sheets

DEVICE FOR APPLYING PRESSURE TO A PERSON'S GROIN

Please notice that this invention is related to some of applicant's pending applications, and the content of the following applications is incorporated by reference as if they were fully disclosed herein. The applicant's previous inventions are as follows: D. Device, Pressure bandages and dressings, D. Device 2, D. Device 3 and D. Device 4.

The application for "D. Device" was applied on Nov. 29, 1991 with Ser. No. 07/800,085 now U.S. Pat. No. 5,263,966.

The application for "Pressure bandages and dressings" was applied on Oct. 28, 1992 with Ser. No. 07/967,379 now U.S. Pat. No. 5,376,067.

The application for "D. Device 2" was applied on Dec. 14, 1992 with Ser. No. 07/989,825 now U.S. Pat. No. 5,423,852.

The application for "D. Device 3" was applied on Apr. 5, 1993 with Ser. No. 08/042,560 now U.S. Pat. No. 5,383,893.

The application for "D. Device 4" was applied on Aug. 21, 1993 with Ser. No. 08/113,652 now abandoned.

BACKGROUND OF THIS INVENTION

Bleeding in a person or patient is a worrisome, bothersome and at times dangerous problem. It can be due to injuries, surgeries or by performing procedures such as cardiac catheterization, angioplasty, the insertion of arterial lines and pacemakers, etc. Many of these cases are subject to complications such as the continuation of bleeding, hematoma, or injury to the wall of artery or vein. In any case, in each one of these there is a need for correction and treatment. This invention is related to the prevention of bleeding in the body after the following events: cuts, wounds, surgeries and procedures in which patients who have had their vessels, arteries or veins canulated for one reason or another (such as during cardiac catheterization, angioplasty, the insertion of an intra-aortic balloon pump, the insertion of catheters for monitoring pressure by arterial or venous lines, angiography of brain vessels or extremities, the insertion of wires or tubes such as pacemaker wires or electrophysiological studies, the insertion of large IV lines or similar procedures, etc. The inventor, like many others, has tried to make a unit to solve this problem and contribute to humanity. His previous applications include D. Device, Pressure bandages and dressings, D. Device 2, D. Device 3 and D. Device 4. In this application, he wishes to introduce a new and improved version of his previous devices in order to make a better and advanced model.

One important issue that is addressed here is the prevention (avoiding) of localized pressure to an artery or vein such as in the application of pressure by fingertips or units with small surfaces. The applicant believes that such a practice not only increases the chances of ischemia in the limb, but also of damage to the vessel walls and blood clot formation (or phlebitis) in the area as well. On the other hand, pressure when applied in the form of a block to the area (as introduced in this application and previous applications of this inventor) will more likely prevent focal pressure to a vessel, leakage of blood and its related problems. Other means of preventing bleeding in different cases are introduced as well. The inventor believes that at this age in the practice of medicine the confinement of patients to a certain position with the use of sandbags, clamps and other similar means is no longer justified and should be avoided due to the fact that it causes the suffering of patients as well as complications due to the lack of activity, such as phlebitis. The earlier the patient is ambulated safely, the better he/she will be.

BRIEF EXPLANATION OF THE INVENTION

In general, these units are to prevent bleeding due to cuts, lacerations or surgery in the vessels, (particularly after interventions in which a vessel of the body is invaded). Basically, these units consist of a non-stretchable, supportive wrap which will hold an inflated balloon or similar pressure-producing means in the area of the wound, (the wound in this text is used primarily to indicate the site of an intervention of any kind, surgical wound or a cut as well) in order to compress the wound area and prevent bleeding. Importantly, these non-stretchable or at times elastic wraps will have a transparent window to allow the wound site to be seen for better and easier care. In many models this transparent area will be made from a hard, clear, plastic to constitute the front part of this unit. This piece may also be made to have a transparent door to allow the front of the wound to be opened and the wound area to be visualized and treated. Importantly, this application introduces the use of multiple balloons for the creation of pressure. Here, a hydraulic system is also introduced for the application of pressure to the wound site. After explaining the basic units, the application continues to show how special units can be made for use in different areas and conditions of the body with more specific details. The use of separable units is also introduced, which will allow one part to be used first and the other later for the purpose of more effectiveness, ease of use and better utilization. These units will also allow the addition of different pieces such as clear or hard walls to the area. Units of different sizes or parts of different sizes can be utilized as well, altogether giving significant freedom of choice. These units will increase the chances of early mobilization in the patients as well, allowing the easy removal of the sheaths from the vessels. Different balloons are introduced to allow many selective jobs to be done, such as pressuring one part more than the other part or pressuring one area or segment while shielding the other area or part as well as pressuring certain areas in different time intervals as well.] The balloons may be chosen to have rigid or semi-rigid pre-shaped parts in their front or back walls in order to allow areas to be pressed in a certain fashion to make a desired outcome more possible. Rigid or semi-rigid parts may be utilized to prevent pressure from only being applied to a small area, if this is not intended to be the case. A shield may be used in order to protect one area or another as well: an artery or vein, particular sheath or one part of the sheath, etc.

THE FIGURES

Copies of previous figures from previous applications are included as a referral.

Brief Mentioning Of The Figures

FIG. 1. This figure shows the side cross-cut view of the simplest model designed to be used in minor injuries.

FIG. 2. Is a bottom plan view of FIG. 1.

FIG. 3. Shows a simple unit with a flat front part.

FIG. 4. A bottom plan view of the unit shown in the previous FIG. 3.

FIG. 5. Is to show a balloon may be part of a circular elastic band in the shape of a ring.

FIG. 6. Shows an end view of the unit shown in the previous FIG. 5.

FIG. 7. Shows a support unit for the upper groin.

FIG. 7A. Is a unit similar to the previous unit, except this one has a balloon, and it is to be attached to the outer surface of the special shorts.

FIG. 8. Is a cross-cut view of the unit shown in the previous figure of 7, showing the position of the balloon placed on the thigh of a patient.

FIG. 9. This figure shows a unit that has a piece for the waist area 623.

FIG. 10. This figure shows the cross-cut view of the unit shown in the previous figure of 9 when it is in place.

FIG. 11. This is a figure to show the general view of the unit shown in FIGS. 9 & 10 when it is in place on a patient.

FIG. 12. This figure shows the strap that is to be connected to the lower abdominal piece 623.

FIG. 13. This figure shows a support unit whose front part 639 will be made from a clear, hard plastic.

FIG. 13A. This figure shows a support unit similar to the previous figure of 13. Except the front piece 639A is to be made from a clear, soft vinyl.

FIG. 14. This is a figure to show the general view of the unit shown in the previous figure of 13 when it is in place on a patient.

FIG. 15. This is a model similar to the previous figure of 13 except this unit has a door made from a clear, hard, material.

FIG. 16. This figure shows the side view of the model shown in the previous figure of 15.

FIG. 17. This figure shows a unit that is to be placed under the back.

FIG. 17A. This figure shows a different model of the unit shown in the previous figure of 17.

FIG. 18. This figure shows a small spring that is to go over the connection part of the two tubes.

FIG. 19. This figure shows the unit mentioned in the figure of 18 placed around the connection part of the IV tubing.

FIG. 20. This figure shows the rear view of the unit shown in the previous figure of 19.

FIG. 21. This figure shows the lower face of this unit.

FIG. 22. This figure shows the side view of this unit.

FIG. 23. This figure shows two tubing of which the connection sided are protected by a hinged spring.

FIG. 23A. This figure shows the side view of a three-way-stopcock which is enhanced by adding a spring.

FIG. 24. This figure is a schematic side view of an inflation bulb that eliminates the need for rotating the valve.

FIG. 25. This is a unit similar to the figure of 24, except the end of this unit has a spring.

FIG. 26. This figure shows a support unit similar to FIG. 13 with a hydraulic unit in its front.

FIG. 27. This figure shows a hard, trapezoidal plastic piece that is to be placed on the wound under the balloon.

FIG. 28. This figure shows a doughnut-shaped balloon.

FIG. 29. This figure shows a rectangular-shaped balloon with an open center connected to an opening.

FIG. 30. This figure shows a balloon that has a rather flat rear surface and a soft, pliable front surface.

FIG. 31. This figure shows a balloon with a protective shield to shield the intra-vascular sheath.

FIG. 32. This figure shows the general figure of a piece of hard, clear plastic that is to press the wound site under the balloon.

FIG. 33. This figure shows the side view of the plastic piece shown in the previous figure of 32.

FIG. 34. This figure shows the front view of the unit shown in the previous FIGS. 32 and 33.

FIG. 35. This figure shows a pair of shorts that will be used for the prevention of bleeding at the time of ambulation.

FIG. 36. This figure shows a person wearing a pair of shorts which have balloons and straps as well.

FIG. 37. The unit shows a pair of shorts that uses inflatable balloons.

FIG. 38. This figure shows a securing method to hold two tubing by an engaging notch 736 to 735.

FIG. 39. This figure shows a notch 738 in a handle that is pushed to engage with another notch on 734.

FIG. 40. This figure is to show the general shape of a tab placed outside of a wrap.

FIG. 41. Shows a hard, clear plastic made from two sliding parts for the front part of a unit for the groin.

FIG. 42. Shows a hard plastic for the front part of a support that has a hole in its front for the tubing of the balloon.

THE DETAILED EXPLANATION OF THE FIGURES

FIG. 1. This figure shows the side cross-cut view of a unit that is the simplest model of these units designed to be used in minor injuries that may bleed. This unit has a clear balloon 601 supported by a band 602 which will hold this unit in place. The band 602 has adhesive layers on its surface, one shown by 603, which are protected by the protected layers of 604 & 605. The tip of the layer 605, (marked at 606) is intentionally longer to allow the easy removal of the protective layer.

FIG. 2. This is the front view of the unit shown in the previous FIG. 1. This figure shows the balloon 601 in the center and the general shape of the band 602. The inner border of the adhesive film 607 is shown, while the protective layers are not.

FIG. 3. This figure shows the side cross-cut view of a unit that is very similar to the unit shown in the previous figure of 1. Except the front part of this clear balloon 603 is flat in order to provide a flat pressure to the area, if that is intended.

FIG. 4. This is the front view of the unit shown in the previous FIG. 3. This figure shows the border of the balloon at 609 and the border of the flat surface at 608. The protective layers are not shown here.

FIG. 5. This figure shows how a balloon may be part of a circular elastic band in the shape of a ring. The unit can be pulled to go over the wound. Importantly, the outer surface of this elastic surface can be taped with non-stretchable adhesive tape to control its length. In this figure, the right border of the balloon is shown by 610 and the elastic ring by 611.

FIG. 6. This figure shows the side view of the unit shown in the previous figure of 5.

FIG. 7. This figure shows the general view of a useful and handy unit for supporting a means of producing pressure in the upper groin area and to some degree in the lower abdomen area as well. This unit can support units such as balloons, fluid filled bags, and screw/lever plate systems as well as other hydraulic means. This unit is of special importance, since it is very compact and can be easily handled. The front part of this unit, shown by 612, will be made from a clear, hard plastic. This piece has an oblique border 613 that will fit the groin line. The lower border is shown at 614. The outer end of this hard piece is to be a means of connection or fastening. In this figure, it is a soft resilient piece 615 which has a patch of Velcro (TM) on it, which is marked at 616. The inner end of this piece 612 is connected to a strap 617, which will wrap around the upper thigh to be fastened to the piece 615. In this model the fastening function is done with a Velcro (TM) patch 619-616 although other means may be utilized as well.

FIG. 7A. This is a unit very similar to the unit in the previous figure of 7. This is to show the general view of a useful unit to be attached by different means (such as Velcro (TM) patches) on the outer surface of a pair of special shorts designed for the prevention of bleeding after the discharge of patients from the hospital. These shorts have one or more pre-inflated air or fluid-filled bags on their front to stand over the wound for the prevention of bleeding in the groin (the shorts are not shown here and were explained in D. Device 2). This unit has the balloon, shown by an X and dash-and-dot line which will be placed over the air or fluid-filled bags covering the wound. This balloon will be inflated manually; if the patient has bleeding and needs more support, this will be a safety means for a patient that is being discharged from the hospital. This option will provide the safety means of allowing physicians and patients to feel comfortable and proceed with early discharges. Importantly, the strap (shown by 617) may be made from a soft part (loop piece of Velcro. (TM)) so that the outside of the shorts will only have the patches of the other part of Velcro (TM) (the hook pieces) and the process will be easy for use. In practice, if the patient notes bleeding, he/she or a companion will inflate the balloon to provide pressure to the wound as directed to have a safer chance of contacting further help and assistance. Importantly, the balloon X and the area over it will be clear, as well as the cover and the balloon under them and on the wall of the shorts.

FIG. 8. This figure shows the cross-cut view of the unit shown in the previous figure of 7, when it is placed on the upper thigh of a patient. In this case it is the right thigh (which is commonly used and please notice that although most models or all of these units in this application are mentioned for the right groin or thigh, it is easy to imagine a mirror image unit that can be made for the left side). In this figure the upper right thigh is shown by 620. The center of the wound area is at 621 and the clear, front piece 612 is shown, which will stand over the balloon (please notice the balloon is not shown here). The side of the lower border of the piece 615 is shown by 622, the piece 618 is also shown.

FIG. 9. This figure shows the general view of a unit that is very similar to the unit shown in the previous figures of 7 & 8. Except in this model, the upper border of the piece 612 is connected to a soft but non-stretchable piece of 623 which has a means of connection to a strap or wrap (similar to the one shown in FIG. 12) that will go around the waist area. In this case it is the Velcro (TM) patch 624. The advantage of having this piece 623 is that it will hold the unit more strongly and sturdily in the area having the lower abdominal piece. Also, the unit will allow a balloon to be placed under this part as well to protect the lower abdomen if the wound or hematoma is expanded in that area. The piece 623 can optionally be made to be clear and have a hard plate of different but proper shape as well. The strap that will be connected to this part is not shown here, but is shown in FIG. 12.

FIG. 10. This figure shows the cross-cut view of the unit shown in the previous figure of 9, when it is placed on the upper thigh of a patient. In this view, only the lower part of the unit is shown. In this figure the right thigh is shown by 620, the left side by 625 and the wound site by 621. The clear, hard piece 612 of this unit is placed over the balloon 626. The end of the strap 617 (which is marked at 618) sticks to the surface of 615.

FIG. 11. This is a figure to show the general view of the unit shown in FIGS. 9 & 10 when it is in place on a patient. In this view, the piece 612 is placed over the balloon 629. The strap 617 goes around the upper thigh area to come around and stick to the piece 615 by a fastening means (here the fastening means is Velcro (TM) patches). The upper border of the piece 612, here marked at 613, is approximate to the groin line 628. The piece 623 is kept stable in place on the lower abdominal wall by the strap 633–635. This strap is connected to the front surface of the abdominal piece of 623 by a matching fastening means which here is a Velcro (TM) patch of 634. The ends of the strap connect to each other by a fastening means which here is a Velcro (TM) patch. The inflation port of the balloon is connected to an inflation bulb 632 and the gauge 631, which may also have alarm components on it, to sound if the pressure dropped.

FIG. 12. This figure shows the strap that is to be connected to the lower abdominal piece 623. This piece will be made from a strap that has a fastening means of 634 (here a Velcro (TM) patch) that will match, fit and connect to the fastening means of the front surface of the abdominal piece 623. The ends of this strap will connect to each other by a proper fastening means, which here is the Velcro (TM) patches 638 and 637.

FIG. 13. This figure shows the general view of a support unit that is different in regards to the fact that it is to hold a balloon which will be placed to stand on the lower abdomen's upper groin side. The front part of this unit is shown by 639 and will be made from a clear, hard plastic. This piece will have the general shape of a trapezoid, having more width in the top than the bottom. The outer side of this will be connected to a soft, non-stretchable piece of 640 covered by a fastening means (Velcro (TM)). The inner upper corner of this front piece will be connected to an upper strap 641 that will go around the waist and whose end 642 is to be connected to the upper, outer side of the piece 639 by a proper fastening means (here by piece 640 covered by the Velcro (TM) patch of 647). The lower end of the inner side of piece 639 will be connected to the strap 643 that will wrap around the upper thigh area and whose end 644 is to be connected to the outer lower side of the piece 639 by a fastening means (here by the piece 640 covered by the Velcro (TM) patch of 647).

FIG. 13A. This figure shows the general view of a support unit that is very similar to the one shown in the previous figure of 13. Except in this model the front piece 639A is made from a clear, soft, strong, non-stretchable vinyl, that is connected to the straps in its three corners by the pieces E, F and G which will allow the U-turn of the end pieces of the straps to occur for easy handling. In this figure, a piece of hard, clear plastic marked by Y and shown with a dashed line will be utilized to fortify the front of the unit. This piece Y may be reversibly connected to the front piece of the unit 639A. In this model, the straps (shown here at 641A and 643A) may be chosen to be made from Velcro (TM) loops, and their end pieces such as 645A and 646A can be made from Velcro (TM) hooks to allow easy attachment and handling.

FIG. 14. This is a figure to show the general view of the unit shown in the previous figure of 13 when it is in place on a patient. In this view the trunk of the patient is shown by 627 and its right thigh by 620. Its left thigh is at 625 and the groin line at 628. The clear front piece 639 is placed over a large rectangular balloon 649. The strap 641 goes around the waist to come around and its end 642 is to be connected to the outer edge of the piece 639 by the piece 640 and Velcro (TM) patches. The inner lower end of this piece 639 will be connected to a strap 643 that will wrap around the upper thigh and whose end 644 is to stick to the lower outer side of the piece 639 by a proper fastening means, here by the piece 640 and Velcro (TM) patches. Again the inflation port of the balloon is connected to an inflation bulb and gauge which may also have alarm components in it which will sound if the pressure drops.

FIG. 15. This is a figure to show the general view of a model similar to the model shown in the previous figure of 13 except this unit has a door made from a clear, hard material in its front that will allow the easy inspection of the wound site and drug application to be done without a need of dismantling the whole unit. This door, shown here by 651, is hinged to the frame by hinges 652 and its lower counterpart. The door goes over the frame and will be locked by a snap 653 that can rotate to lock or release the door. The inner border of the frame can be seen through the clear door, marked at 650.

FIG. 16. This figure shows the side view of the model shown in the previous FIG. 15. In this view the lower side of the frame is marked at 649, which is connected to the groin strap 668 at its inner end 667. The end of the groin strap 668 is marked at 644. The outer border of this frame is connected to the piece 640, which will have a fastening means to connect to the piece 644, [here a Velcro (TM) patch]. The door is marked at 651 and is connected to the frame by the hinge 652. The snap 653 is held in place by a small pole 654 that is connected to the frame.

FIG. 17. This figure shows a unit that is to be placed under the back and has multiple functions. First, it is to allow the strap or wrap to move easily inside the tunnel 656 and to avoid the need to bother the patient for moving the strap. Secondly, it will support the back by having a soft pad or properly shaped material stuck to its surface on the Velcro (TM) patches of 659–660. This unit will also allow a means of heating to be placed over this unit to provide better feeling to a sick patient that has to remain on a hard, uncomfortable X-ray table. This unit will also hold an inflatable balloon that can be placed over it to provide a proper size support to the patient's back. Importantly, all of these units are to be made X-ray transparent, unless they will be used only after the procedure. In this view, the tunnel 656 is created by having two walls that come toward each other, but do not attach to allow the easy insertion of the strap inside the tunnel to occur. Then the door 657, which is hinged to the bottom of the unit at 658, can be closed to keep the strap or wrap inside and prevent friction. The upper border of the unit is shown by 655. This heating unit may be a balloon filled with heated water, fluid or an electric heating pad if circumstances allow.

FIG. 17A. This figure shows a different model of the unit shown in the previous FIG. 17. Except this unit has the pieces 708, 709 that are different. Their opening is not in the center, and shows how these pieces may be made to allow the easy insertion of the strap inside them (through the opening between them). Then the strap can be held safely inside to allow easy motion without being pressed by the upper surface of the mattress or table cover. This unit also shows an appropriately shaped and sized balloon marked at 710 (by dashed line) that is incorporated in the front wall of this unit and can be inflated by a bulb to provide support and safety to the patient. These units will be made X-ray transparent to allow them to be used on the X-ray table. They will provide comfort to the patient and be ready for use in the placement of the device for the prevention of bleeding.

FIG. 18. This figure shows the general view of a small spring unit that is to be placed over the connection part of two tubes used in this unit. When in place, this unit will prevent these tubes from being disconnected accidentally. This figure shows the back wall of this unit at 661, the upper pair fingers at 662, and the opening between these fingers by 664. The lower pair of fingers are shown by 663. Importantly, the inventor wants to indicate that this unit may be made to have one pair of its end pieces hinged to one side of the tubing to allow a much easier connection to occur, so that one end can thus be placed inside the other end and the spring can be snapped on to its side.

FIG. 19. Shows the unit mentioned in the previous FIG. 18 in place around the connection part of the tubing of this unit, any IV or similar tubing. In this view, the main wall of the spring is shown at 661, the upper fingers by 662 and the lower fingers by 663.

FIG. 20. Shows the rear side 661 of the unit in place. This figure may also be used to show that this unit may be made from a clear material such as plastic with a spring type function.

FIG. 21. Shows the lower face of this unit.

FIG. 22 shows the side view of this unit.

FIG. 23. Shows the side view of a connection site of two tubing where the connection is protected by a spring 669 which is hinged to one end 666 at 670 and goes over the end of the other side 665 by its free end 671. The free end is intentionally curved to allow an easy removal by pressing figures so as to not hurt the person's fingers.

FIG. 23A. Shows a side view of a three-way-stopcock. This three-way-stopcock is enhanced by adding a spring similar to the one shown in the previous figure so that the spring will make the connection of the three-way-stopcock to the female end of the other tube stable and protected. It would be easily possible to have the spring protection on both ends of the three-way-stopcock; however, since the male end of the previous tubing may have the spring, it will compensate for this action.

FIG. 24. Is a schematic side view of an inflation bulb that has a different structure which will allow easy usage and eliminate the need for the rotation of the valve in commonly used bulbs. It will also allow parts to be made from plastic and be cheaper; importantly, this unit can be covered by a clear disposable plastic that will go over it and be disposed after use to provide sterility. In this unit, a rigid tube 682 has two connection sides: 674 (for the elastic bulb) and 673 (for the next tubing connected to the balloon). The tube 672 has a hole 680 with a rubber or latex piece 678 sitting on it, which will fit inside and close it tightly when pressed. The piece 676 is to function like a lever. It has the end 677 connected to the piece 678 to raise it up when its other end 676A is pressed down by a finger. The elastic tubular piece 679 goes around the piece 677 as well as the end part of the rigid tubing 672, so that its elasticity will hold the pieces 677 and 678 in place, closing the hole 680. Pressing the bulbar end 676A will cause its other end 677 to be raised, allow the air to escape and the balloon to deflate in a controlled fashion. Point A shows a spot which may have a one-way valve of any kind to be constructed to prevent the air from going inside the balloon. This valve can be a small disk inside a space to move back and forth to close the rear end when air moves back, or any other smaller valves.

FIG. 25 shows a unit similar to the one shown in the previous FIG. 24, except the end of this unit is fortified by a spring to allow a secure connection to the end of the other tubing to occur. In this figure, the spring (spring means) is shown by 681 and its hinge at 682. Importantly, the free end of this spring may be modified to work in commonly used IV tubing and similar units as well; also, this spring may be made from plastic material as well, with some extensibility.

FIG. 26 shows the general view of a support unit that is basically similar to the unit shown in the previous FIG. 13, except this has a front piece 683 made from a clear, hard, plastic which can be held in the groin area (or any wanted place) by straps similar to the ones shown for the previous figure of 13. One goes around the lower abdomen and the other goes around the upper thigh area to hold the front piece sturdy and in place. This front piece will hold a hydraulic unit in its front/center part that consists of a cylinder 684 that has a piston 685 inside it. The other end of the handle of this piston, marked at 686, will have a round piece 687 which will fit and be placed inside a matching round cradle 690 from a flat piece 689. This construction will allow the piston to be moved by the alteration of air pressure inside it by the bulb 632 and its inner pressure can be monitored by a proper gauge 631 as well. The pressing function of the piston will press the piece 689, a charged balloon, a fluid-filled bag or their combinations on the wound site to prevent bleeding.

Figure 30:
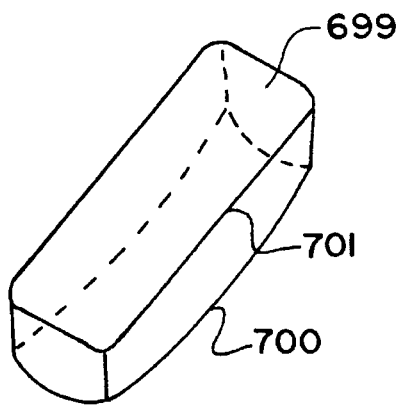

FIG. 30 shows the general figure of a balloon that has a rather flat rear surface marked at 699 with its side border marked at 701 and its lower side border by 700. The front face of this balloon that will stand against the wound will be soft and pliable to allow it to assume the shape of the area and fit the spaces between the sheaths or tubes connecting to the skin, etc. This balloon may be pre-inflated as shown in this picture or have an inflation tube to allow it to be inflated to apply more pressure to the wound site.

Figure 31:
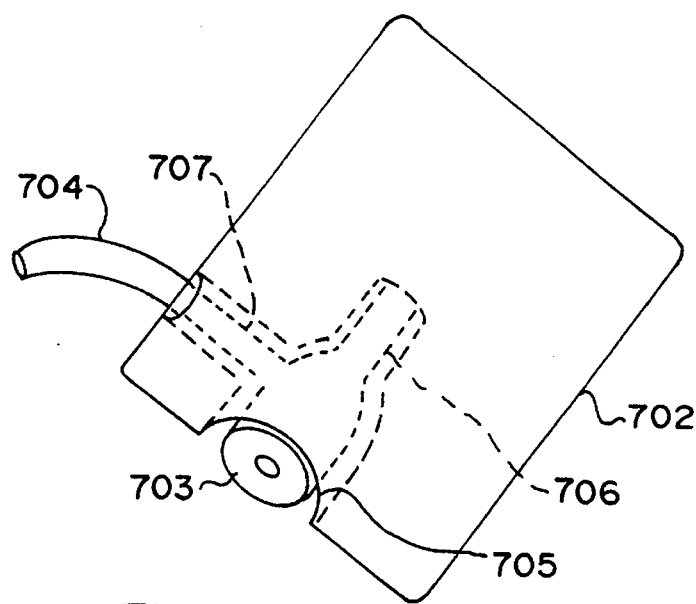

FIG. 31 shows the general figure of a different balloon 702 that has a rather flat shape and can be pre-inflated or inflatable. However, this unit has a protective shield 705 that is to protect the unit under it, which here is the intra-vascular sheath 703 with its side tubing 704. The function of this shield is to protect certain areas or parts which should not be pressed, such as the beginning of the tube of the sheath 706, its IV site as well as its body 703. The shape of the shield may be different in different uses and models.

Figure 32:
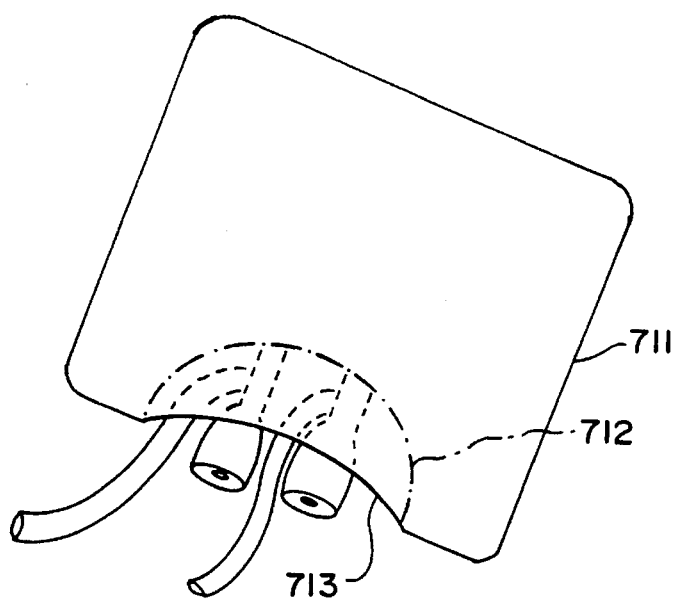

FIG. 32 shows the general figure of a piece of hard, clear plastic that is to press the wound site under the balloon. However, this piece has an area 713 that will shield the base of the sheaths and prevent them from being pressed on the skin by the balloon, if they have to stay inside the wound area. This unit (marked at 711) has a raised part 713 which is like a part of a dome. 712 shows the connection line between these two areas.

Figure 33:

FIG. 33 shows a side view of the unit shown in the previous FIG. 32. In this figure the body of this piece is shown at 711, the raised part at 713, and the connection line between these two areas is at 712.

Figure 34:

FIG. 34. This figure shows the front view of the unit shown in the previous FIGS. 32 and 33. In this figure, the body of this piece is shown at 711, and the raised part at 713, the space under the dome 713 is also illustrated.

Figure 35:
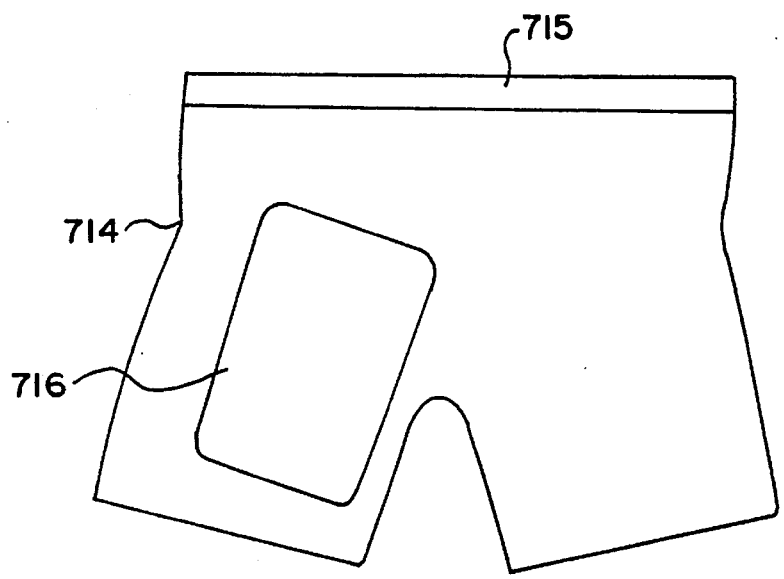

FIG. 35 shows the general appearance of a model of shorts that will be used for the prevention of bleeding at the time of discharge. In this figure 715 shows the upper border and the elastic ribbon of the shorts. 716 shows the clear front window of these shorts.

Figure 36:
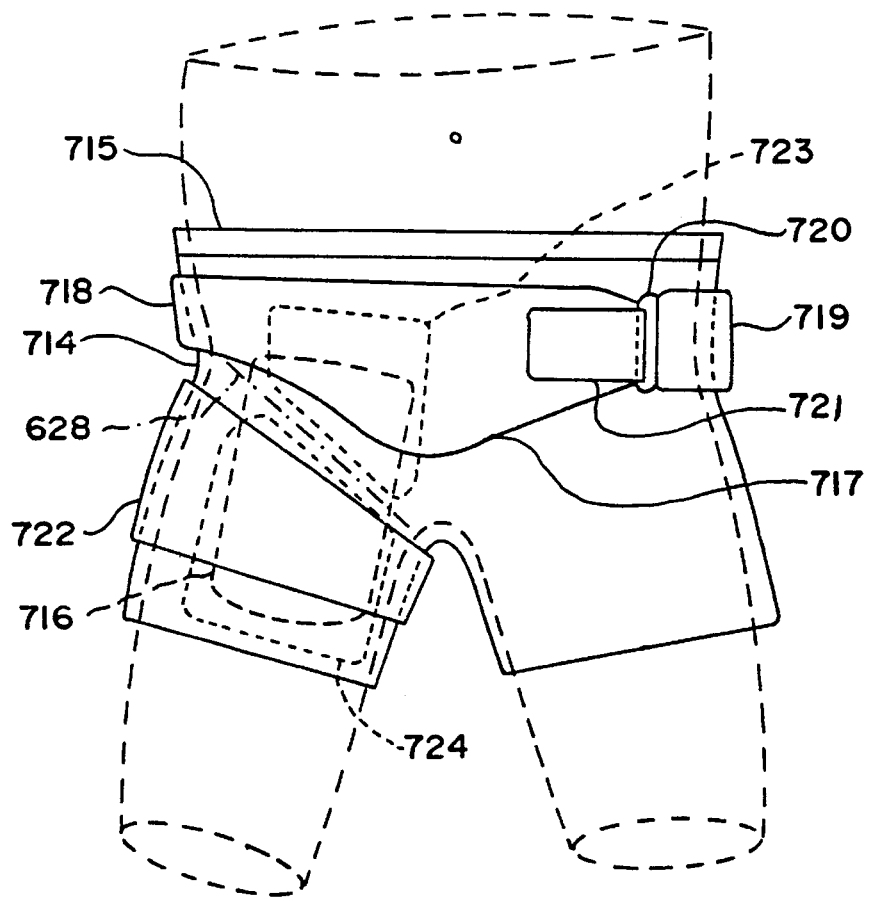

FIG. 36 shows a person wearing a pair of shorts similar to the one shown in the previous FIG. 35, except in this figure the balloons are also shown by dotted line, one at 723 for the lower abdomen and one at 724 for the upper thigh as well. In this figure the upper border of the shorts is shown at 715, and the groin line at 628. The border of the clear window of the shorts is shown with dashed lines at 716. This figure also shows two specially shaped supporting non-stretchable straps/wraps that go around the lower abdomen and upper thigh area. These will be tightened securely to hold the underlying balloons in place for further application of the pressure in the wound area by different means, such as the inflation of the balloons. In this figure, the mid portion of the lower abdominal strap is shown at 717 with its right border at 718. The continuation of this wrap comes around the back and is shown at 719. The end of the piece 719 has a snap shown at 720. The left end of the front piece, marked at 721, comes through the snap 720 to make a U-turn and be attached to its own rear surface by a fastening means (here Velcro (TM) patches are used). The strap for the upper thigh is shown by 722 and will wrap around the upper thigh. The ends of this strap will be fastened by a fastening means. Here, Velcro (TM) patches are used, which are not shown in the picture.

Figure 37:
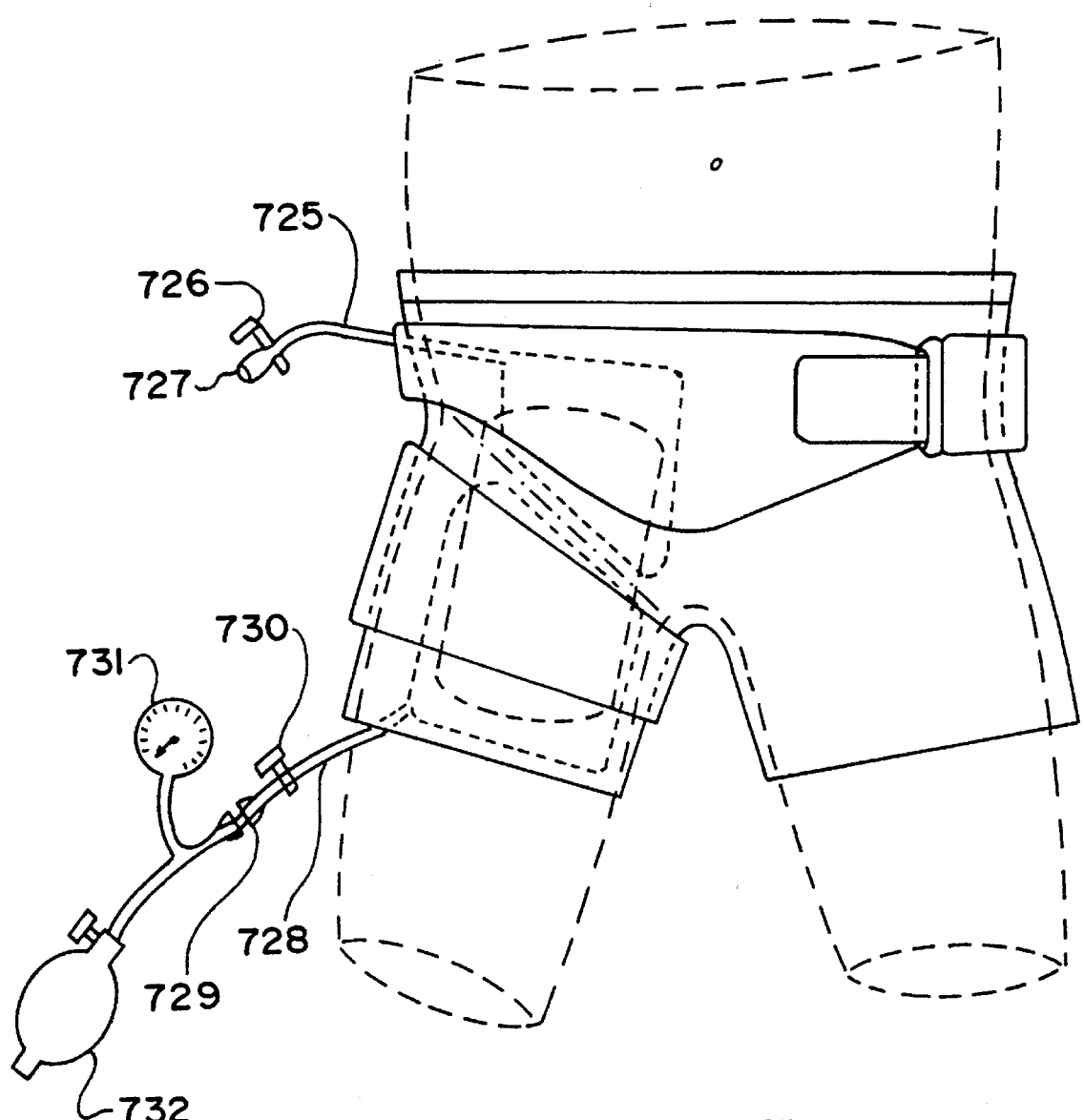

FIG. 37 shows a unit that is basically very similar to the previous FIG. 35, except in this unit, the balloons are inflatable and their pressure can be adjusted. 727 shows the opening of an inflation tube for the balloon in the lower abdomen area and a valve 726 for closing it. The inflation tube of the balloon for the upper thigh area is shown by 728 and its opening by 729 and it has the valve 730 to close it. In this figure, the inflation bulb 732 and its related gauge 731 are also shown. These balloons can be used selectively; for example, the balloon for the lower abdomen may be eliminated if there was no need for it.

Figure 38:
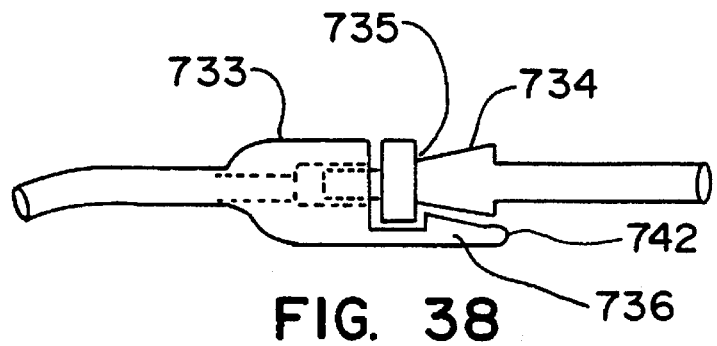

FIG. 38 is schematic to give a general idea about a method for securing the connection part of two tubes used here for the inflation tube and the inflation bulb or gauge. When in place, this unit will prevent these tubes from being disconnected accidentally. This figure shows the female end of one tube at 733 and a specially shaped male end of another tube at 734. The end 734 has a notch type figure (shown at 735) which will engage with a piece 736 that has a notch to fit the matching notch 735. The tubes can be separated by moving the piece 736 away by holding its specially shaped (somewhat rounded prominent) tip 742.

Figure 39:
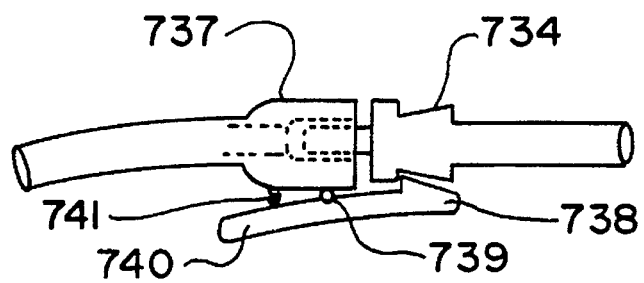

FIG. 39 shows a unit similar to the one mentioned in the previous FIG. 38, except in this unit the piece responsible for holding the end 734 has a handle 740 hinged at 739. This handle is pushed away by a spring 741 which will hold the tip 738 in a position where it will be pushed toward the end 734. These tubes can be separated by moving the piece 738 away, which is done by pressing the piece 740 which will function as a lever.

Figure 40:
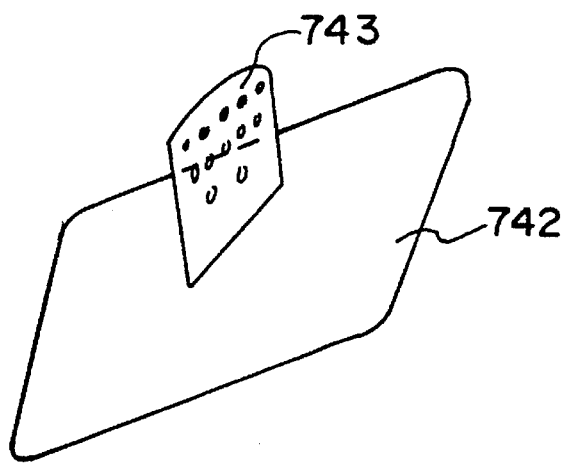

FIG. 40 is to show the general shape of a tab placed outside of a wrap. The wrap is shown in 742 and the tab at 743.

Figure 41:
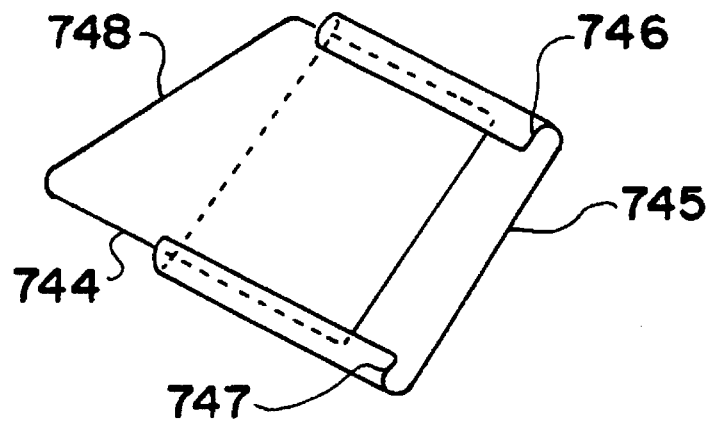

FIG. 41 is to show a hard, clear plastic for making the front part of a unit that is to be used for support in the groin and upper thigh areas. This unit consists of combinations of two parts: one part, marked at 744, which slides inside the other part 745 which also has two twisted sides 746 and 747 that allow the sliding function to occur in order to allow the size and length of this unit to be changed easily. The border 748 is oblique to fit the groin line in the right side.

Figure 42:
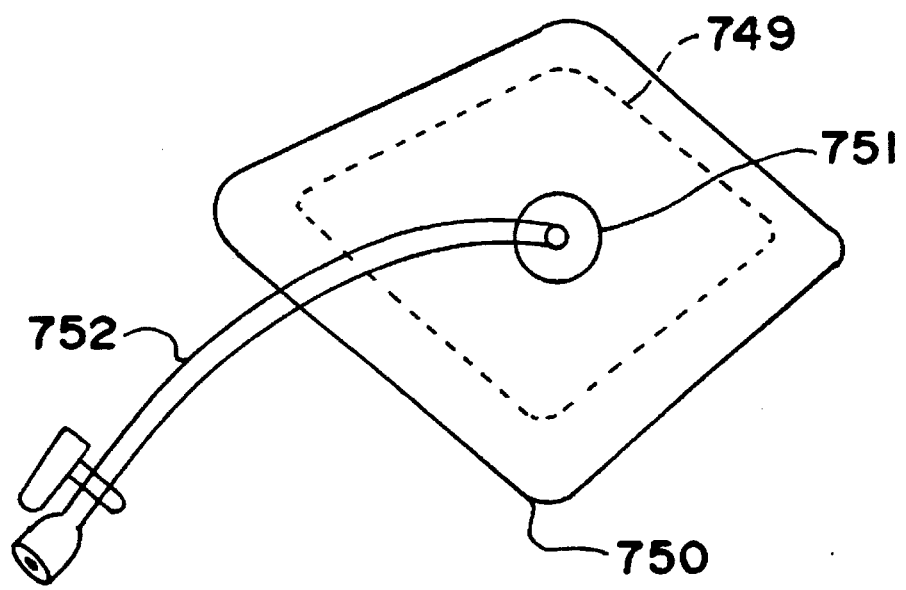

FIG. 42 shows a hard, clear plastic for making the front part of a support unit or to be used with it. The plastic has a hole in its front that will allow the tubing of the balloon to go through it. The hole may be larger than the size of the tube to allow adjustment to be done and may have a circular, oval or similar shape. In this figure the hard plastic piece is shown at 750 with its front hole at 751, the balloon at 749, and the inflation tube of the balloon at 752. This method also may be used with supports as well.

DETAILED EXPLANATION OF THIS INVENTION

Bleeding is one of the serious problems that occurs to mankind. It is a cause for concern and fear, a cause of weakness and shock, and if it is severe and is not treated, it can easily kill a person quickly. In fact, this has been a very effective way of killing people or animals: "bleeding them to death". For this reason, bleeding is to be stopped in almost every occasion; many plans and attempts have been made to prevent it and its related problems. In general cuts, wounds and injuries are the main causes of bleeding; however, many procedures in which a vein, artery or an inner part of a human being or animal is cut or invaded can also be a main cause of bleeding. This is also true about the use of certain medications such as anticoagulants: Heparin, Coumadin and very powerful new thrombolytic agents used in conditions such as heart attacks and blood clot formation in the lungs can cause it. The leakage of blood outside and in the vicinity of the procedures also occur, and trauma and injury to the wall of the vessels cause changes in color and shape of the area, (so called echymosis), hematomas and even A–V fistulas. Besides these, the psychological reaction and concerns of the patients, their relatives and the medical staff are also very important as well. These problems all come one after another, one way or another and deserve special attention to prevent physical, psychological, economical or medico-legal complications. One very important and major intention of this applicant is to introduce a means of preventing damage to the vessels, which many times are small, hard to see or detect by the present practice of medicine. In the mind of this inventor the methods which have been used to prevent bleeding in such conditions have not been satisfactory. The means that are commonly used such as the application of bandages, adhesive materials and sandbags have their own problems of being less effective as well as having their own side effects. These problems have been addressed in more detail by this inventor in his previous applications referred to earlier, and his previous inventions have offered a means for preventing those problems. He has pointed out that in the methods that are commonly used (such as heavy bandaging of groin and using sand bags in that area) not only is it difficult to measure or control the pressure applied to the wound, but also the use of adhesive materials is problematic due to skin reactions, pulling hair at the time of removal, etc. The units which he introduced before solve many of such problems, and although in his previous applications the use of transparent windows for the evaluation of bleeding has been offered, in this application this issue is particularly stressed in order to maximize their use. The use of clear windows will decrease and eliminate the need for a medical personnel to open the wound site for observation. In this application, an attempt is made to make the units more simplified. In this application, the prevention of bleeding starts with an introduction of the simplest and most basic unit which is a pressurized adhesive strip. In such cases a Transparent Pressurized Balloon will be incorporated in a unit similar to commonly used adhesive strips to make a unit that is clear and transparent (at least in its very center) so that not only will it provide the needed pressure to the wound area, but also importantly it will allow the wound site to be monitored easily and the person to notice if the bleeding continues. This unit can be made larger to be used in larger areas as well. Importantly, such a support unit may have a number of tabs of different shapes, size and natures on its outer surface to allow the tabs to be pulled, stuck, or tied to each other or the sides of the support unit to help in controlling the shape and length of the support units. These support units may be made from an elastic material such as latex, that will accept the sticking or attachment of non-stretchable tapes to enhance their effectiveness, versatility and comfort. So that in general, it will allow a very valuable unit to be made for solving a major problem in human beings: "wound bleeding." This will be useful for the prevention of bleeding or oozing secretions after certain surgeries or wounds, etc. In such cases, a combination of controllable pressure and dressing may prevent or diminish the swelling and disfiguration of the wound site and the area. The fact that the temperature of some units may be changed may be quite helpful as well. This can be done by the use of a fluid filled balloon or even with the use of an electrically heated pad which can be incorporated in the support units as well. The clear units, balloons and bags will add a very important value to these units in providing an easy means of observation. The use of doors will be very useful to allow the direct inspection and treatment of the area. The use of secondary units for the prevention or controlling of bleeding during dressing, etc., can be of tremendous help in many battle wounds. Importantly, the shape of this unit may be modified to match the shape of the different areas of the body in which such protection is needed. For example, a unit for the subclavian area may be made. It is important to notice that the subclavian area is lower than the surrounding area, when compared to the wall of some areas of the abdomen that are usually higher than the surface of the wound area. Thus, it would need a modification of this unit to fit the area. The balloons or pressure-producing units will be held in place by a non-stretchable or even elastic support unit. One larger group of these units will be made from a non-stretchable support unit that will hold a balloon or a bag in place securely. The balloons or bags may be pre-inflated or can be inflatable. In some cases, they may even be filled with fluid or water. The fluid may be heated or cooled to provide the application of needed temperature to the wound area. These units may constitute of a layer of gauze of different thickness on the front as well as to absorb blood or provide softness, sterility or medication. This gauze may have a clear plastic in its rear surface to prevent the transpassing of blood and secretions to the balloon side.

For general use, a clear suitable balloon may be made to be held in place by either having a rim or end piece with adhesive materials in order to stick to the skin or by using a unit in the shape of a ring or strap of elastic to go around the area as was previously suggested by this inventor.

This basic unit may be made in many different shapes and sizes to allow it to be used in many conditions and places (such as the hands, arms or leg wounds) or after surgeries and in any other similar conditions, such as hernias. In some models the rear surface of such units may be made with a piece of hard, transparent plastic or similar materials to allow the pressure in the wound area to build up. Importantly, the shape of this hard, transparent plastic may vary; it can be circular, rectangular, oval, irregular or any other needed shape. This hard piece may be made to be curved such as concave, convex or specially shaped or with special curves in order to match the shape, curvature and anatomy of the part of the body in which they are to be used. The borders or edges of this hard, clear plastic piece may be thicker or bent for better use. This piece will be held in place by a support unit which may be made from a non-stretchable or elastic material depending on the area or size of the unit and the circumstances in which it is used. For example, in smaller units for the fingers and limbs in which a higher pressure is not needed, the wall of the support unit may be chosen to be elastic, although it may be non-stretchable as well to pull the sides of the balloon toward the skin. In larger units, the support unit will be made mostly from a non-stretchable material. Importantly, the balloons and bags will be transparent as well so that the combinations will give the chances of a better visualization without a need for removing dressings. A lens and an electrical operated bulb may also be incorporated for a better observation in certain cases. For example, a wound in a soldier wrapped in the middle of the night in a jungle cannot be seen easily unless it is lighted and he may not be able to hold the torch. However, a lighted wound can be checked easily in these circumstances.

On the other hand, the support which such units provides will allow early ambulation to be possible, which is very important. It is important to notice that making patients stay in one position is many times very uncomfortable and should be avoided at all cost. This application also mentions models in which an air, fluid, or gel-filled balloon or bag may be used in the wound areas. It is also to be considered that a force generated by a spring, screw or lever system may be utilized to apply pressure to the site of the procedure. This application introduces a hydraulic means that will provide the needed pressure for application in the wound site as well.

So, in general, this unit consists of a supportive wrap, which supports a pressure-producing means such as balloons, screw/lever plate systems or a hydraulic means and related materials which will be explained in more detail.

The Support Units: The Bands, Straps And Wraps And Their Specifications

The support system is basically to provide the needed support for the application of pressure to the wound by different means. This may also be referred to alternatively as "the wraps" as well. Primarily, the technique mentioned here utilizes bands, straps and wraps (from here on they all may be referred to as "wraps") to hold a bubble, balloon, fluid-filled bag, screw/lever plate system, hydraulic system or any other pressure producing means of creating pressure in the wound area. These bands, straps or wraps may be made from an elastic or non-stretchable material depending to the model that needs to be used. The reason for the choices are as follows:

A. The elastic bands, straps or wraps will be primarily used when the bubble or balloon (from hereon may be referred to as a balloon) is pre-inflated or fluid-filled. In such cases the elasticity of the unit will pull the balloon against the wound to create pressure in the area. Primarily, this will be in those cases in which the need for pressure is not high and the pressure in the area does not need to be changed much. The ends of these units or some parts of them may be made from a non-stretchable piece.

B. The non-stretchable bands, straps or wraps (from here on they may be referred to as "wraps") will be mostly used when the need for pressure is higher and the pressure means is to be supported strongly. This may occur in arterial bleeding, in massive wounds, when the pressure inside the body is high or can increase to cause bleeding (such as with intra-abdominal pressure), during coughing or vomiting, etc., and similar conditions.

C. In some models the combination of these two materials may be used for the best function as desired. The inventor has introduced a special type of this combination in which the main unit will be made from an elastic material. However, there can be combinations of non-stretchable materials as well that would allow different units to be made from them. In such cases, the elastic parts will pull the unit and allow softness in accepting shapes when the non-stretchable parts prevent length extension.

Importantly, tabs will also be used and placed outside of the wraps to allow the wraps to be pulled and positioned as required. In such cases, the outside surface of these wraps in certain places or throughout the unit may have tabs of different natures in order to allow them to be held to pull the underlying wall easily from the skin in order to adjust their position with ease. Furthermore, these tabs may also be made to be pulled, connected or taped to each other or the outer surface of the wrap in order to adjust the length of the wraps. This was previously explained in the inventor's previous application of D. Device 3. The advantages of making the unit from latex were explained in D. Device 3, which is for the unit to allow the non-stretchable materials such as adhesive tapes to be stuck to it to control the length of the latex under it in an attempt to control the overall length of the unit. Importantly, the use of such tabs is so beneficial that even the non-stretchable wraps may be made to have such tabs on their surfaces in needed areas to help in handling and positioning.

These wraps will be made to match the shape, size and anatomy of the area or the wound site. In one major group of models, this support will hold one or a series of special balloon or bubbles in the intended area.

Figure 1:
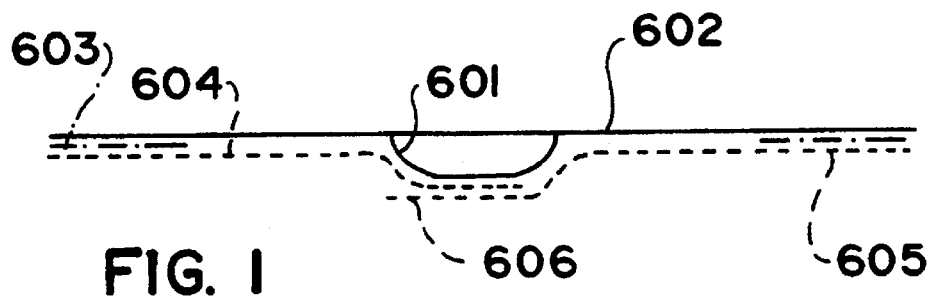
Figure 2:
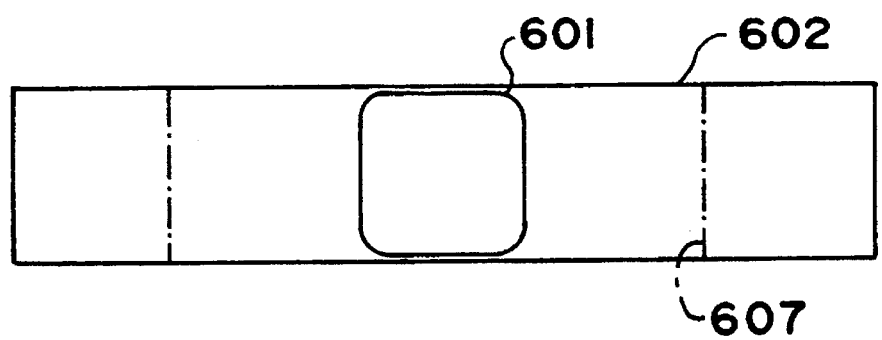
Figure 3:
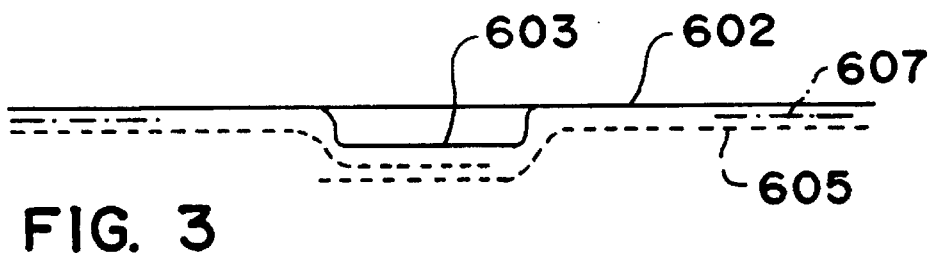
Figure 4:
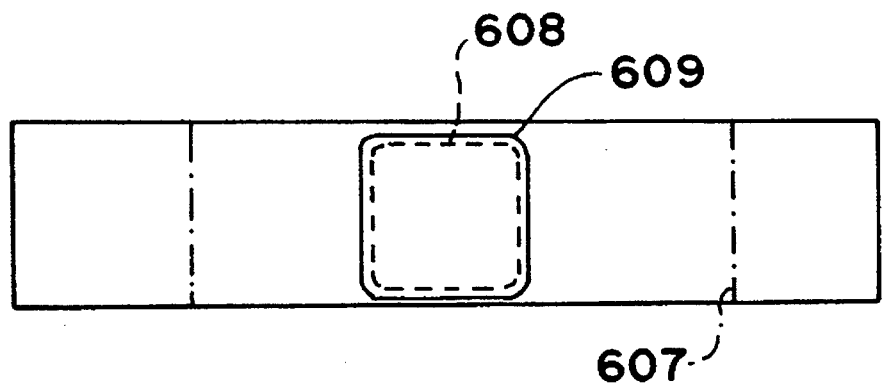
Figure 5:
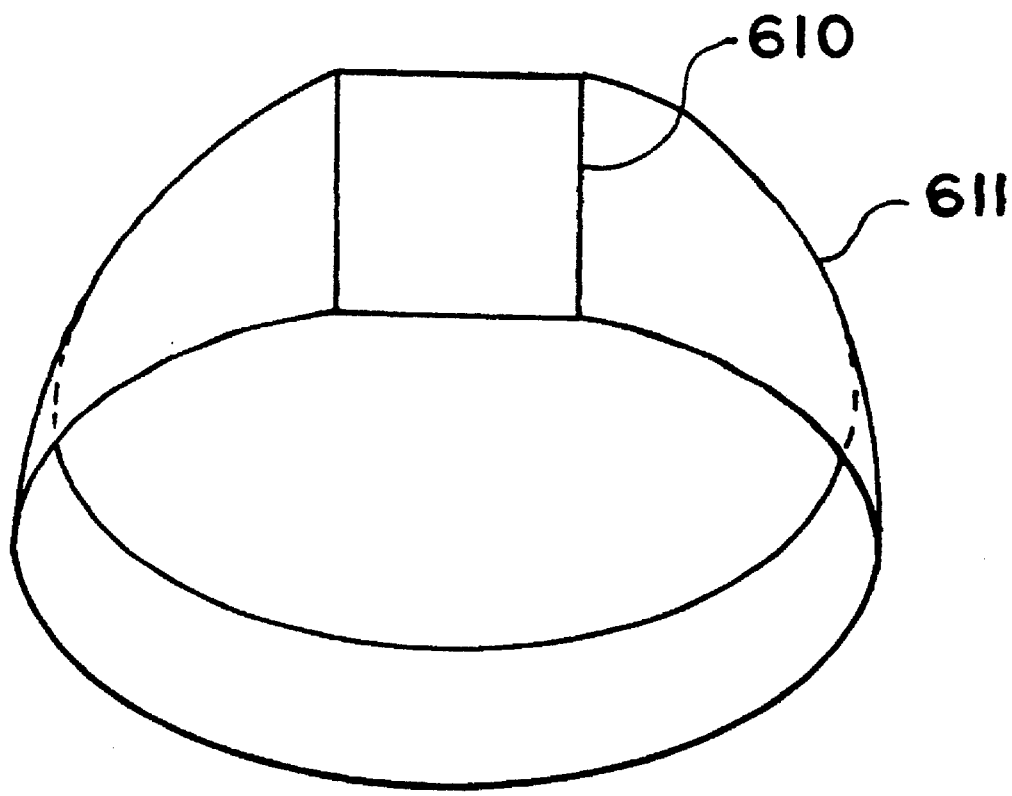
Figure 6:
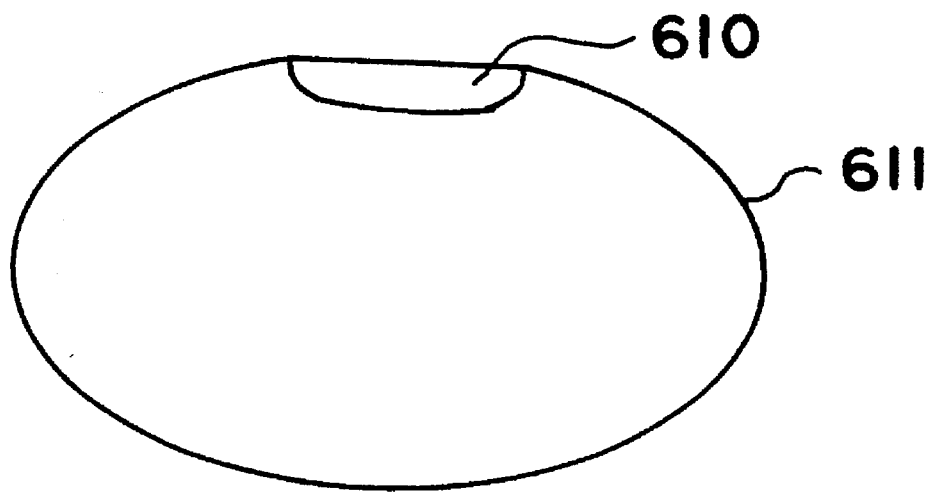
Figure 7:
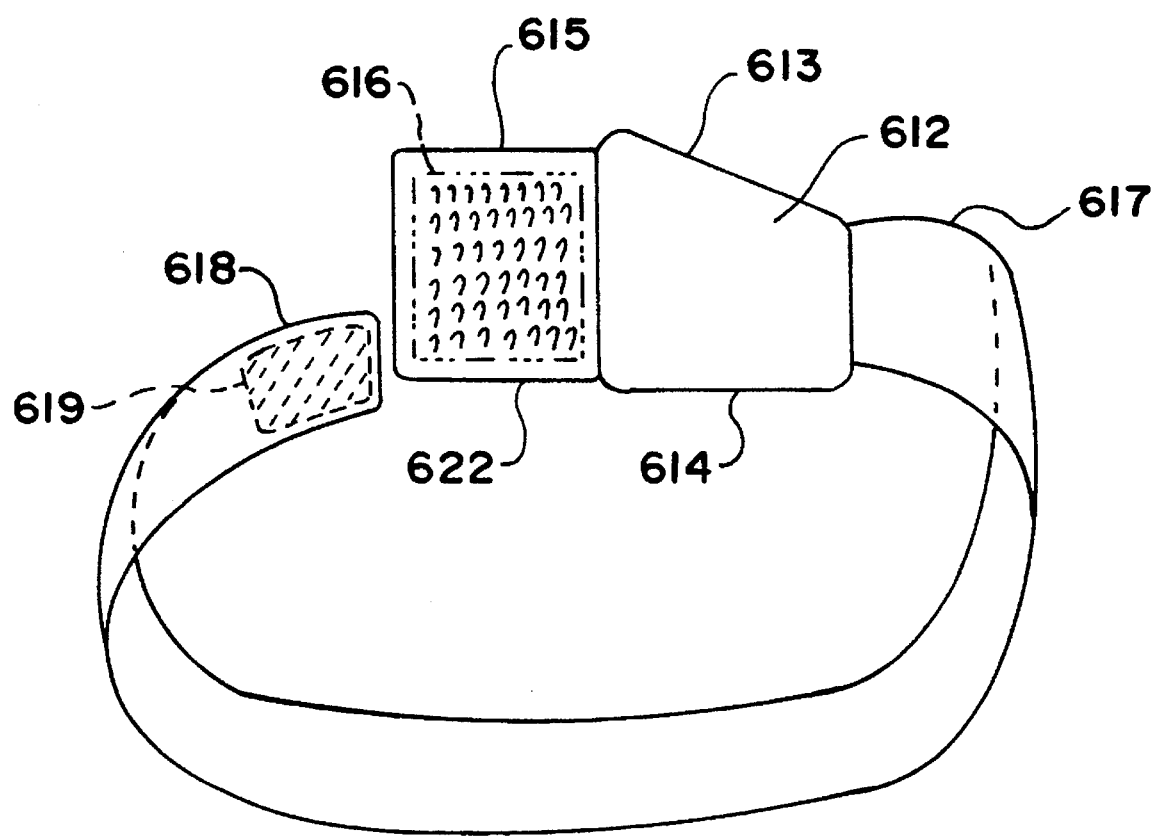

These balloons will be held in the area with one of the following methods:

1. Using a ring of elastic with variable width (FIGS. 5 & 6) and strength such as a band, strap or wrap. In this model, this ring will go around the area such as the finger, wrist, arm, limb and trunk, etc., so that the elasticity of the wrap will press the bubble or the balloon toward the wound.

2. In one group of models, the balloon will be in the center or the front surface of a wrap which has two parts, one on each side of the balloon. These parts will be wrapped around the limb or wound area for their ends to be joined and stuck to each other by utilizing a fastening means to hold the wraps in place securely. A narrow band of adhesives may also be placed in the rim and around the periphery of the wrap to make the wrap stick on the skin with more security. Importantly, even in smaller units, the balloon may be separate, with the strap allowing the use of different balloons with the strap to be possible.

3. Adhesives may also be applied on the surface of the end pieces of the wrap (FIGS. 1 to 4). In this case a film of adhesive on the surface of the end pieces of the wraps will be covered and protected by a layer of plastic that will be peeled off at the time of use. The person may stick one end of the wrap in place, making the other end stick to the rear surface of the previous end. In some models, it may be stuck in part to the skin as well, for better stability and also in preventing the unit from slipping and sliding over the wound area. Importantly, all these bands, straps or wraps may have lines, marks, shapes and figures or similar informative materials on them to allow the better placement, directions and usage of these units. These units may have different coloring for simpler and better usage. They may be made to be cut down to size as well. In a sense, these will be improvements on the previously applied pressure bandages and dressings. The wraps may have small stitches placed to shorten the length of the wrap and be removed when needed to increase the length of the unit. The units may have tabs on their outside surfaces to allow better positioning. The tabs may also be pulled and stuck to the surface of the wrap with adhesive tape to participate in the tightening process. The rear surface of these wraps may be made to allow the use of adhesive tapes for further security.

4. A Velcro (TM) system may be used for the connection of the end pieces of these units, which will be conveniently placed for this use.

5. Any other means of fastening such as snaps, buckles, the use of plastic or molded pieces, adhesive taping and similar methods may also be used for the purpose of connecting the end pieces of these wraps together.

The face of the balloon may have an area of sterile gauze protected by a removable plastic cover to be peeled off at the time of use. Importantly, these gauze may be pre-medicated as well to allow better and faster usage, since many times the need for medication is urgent when the unpacking and application of medication may not be easily done. It may not even be practical or economical to buy one whole tube of medication for a single possible urgent use. Even if the medication and tubes are available, their preparation needs two clean and properly functioning hands, which may not be available all the time, especially when the person is alone and the hand is injured, in pain or shock. Therefore, in such circumstances, the use of rings with medicated gauze on them or balloons with medicated gauze such as disinfectants (or other needed medication) would be of great help. Clear windows (and in some cases open windows) may also be utilized and are believed to be very important in saving the time and energy of medical staff. The wraps will be made from a non-stretchable material. Disposable units would be of main interest to prevent contamination. Also, latex, rubber or similar materials may be utilized with a design to match the curves, boundaries and uneven shapes of the area. The support units will be shaped to fit the curves of the area and hold the balloon inside or under their inner parts securely. The edges and borders may be curved or can have elastic bands or a means of holding the unit and balloons in place safely and securely. The ends of these support units will wrap around the limb or body part and be attached to the other part (or its own end) to make the circle complete for a secure, sturdy, unit.

Importantly, the use of pieces of special transparent plastics will be of main interest in observing any potential bleeding. These pieces may be hard and specially shaped to match the shape of the area. These pieces may be part of the wrap or they may consist of the front piece of the unit and be held in place by straps. They may be constructed to have different desired shapes or may be made from pieces that fit each other in order to allow them to be pulled to expand or be squeezed to retract.

In some models the wrap may be fortified by the use of a piece of hard material in its body in front of the balloon to support the pressurized balloon or bag. This hard, clear piece may be part of the wall of the unit, or separate and placed inside a pocket on the wall of the wrap or attached to the wall of the wrap by different means, such as adhesives, Velcro (TM) patches, snaps or similar attaching means. The advantage of such a method is that it will allow different shapes, sizes or consistencies of these support pieces to be utilized. Furthermore, when desired, the hard pieces can be exchanged or removed, to stay out of the way and not limit the motion of the patient.

The clear windows may be made from soft plastic as well. The whole wrap may be made from a clear material such as latex, vinyl or different polymers. A combination of materials may be used, such as soft absorbent fabric linen with vinyl, polymers or fortified latex, which will allow the construction of a unit that has a soft and fluffy inner cover made from soft fabric, with the outer layer being strong enough to support a pressure-producing means. Alternatively, a softer clear outer wrap (such as latex) may be attached to an inner fabric which is soft and comfortable but also strong and non-stretchable. The sizes, thickness, shapes, coloring, and consistency of the wraps throughout the unit and the other characteristics of these units may vary to allow different units to be made to fit different people with different needs. A unit made from latex or a similar material will allow sticking a non-stretchable adhesive tape to the surface of the unit, making the unit less stretchable and more tight. This will prevent the patient from being bothered by adhesive tapes stuck to their skin. Importantly, a non-stretchable material may be reversibly stuck to a stretchable layer to allow the length of the underlying part to be changed favorably, which provides a great option. This was introduced in length in the inventor's D. Device 3.

The sticking or fastening of the ends of these support units or wraps may be achieved by utilizing the following methods:

a. Adhesives may be utilized to stick one end of this unit to another.

b. The use of Velcro (TM) patches, loops and straps for this purpose to allow easy connections of the ends.

c. The use of different means and methods of fastening such a belt system and appropriate buckles, snaps or any other similar means. These pieces will be made to allow the strap to be reversibly held in place securely and its length to be adjusted as well.

d. The use of adhesive tapes that will go over the ends that are brought adjacent to each other.

e. Any other means of reversible connections may also be used to allow the ends of these straps or wraps to be held together easily and reversibly.

Importantly, these wraps may be made with openings in certain areas of the body to make a better or more comfortable unit. These openings may be made in the prominent sides of the hips, in the tip or prominent sides of the elbows, in the shoulder or in any desired area.

These openings may play different roles; for example, they may allow the evaporation of sweat, a joint to move more easily or even the unit to be stabilized in the area more securely.

The connection of the balloons and wraps may be permanent or reversible.

A. In cases with permanent connections, the balloons will be permanently attached to the wrap by one means or another (such as the use of adhesives, sewing, sticking, etc.) or may even be constructed to be part of the wrap as well.

B. In temporary connections, the connection of the wraps and balloons will be temporary or reversible. This may be achieved by the use of one of the following means:

1. The use of adhesives of different strength. In such cases the use of weaker glues will allow them to be detached and re-attached.

2. Velcro (TM) patches.

3. Different snaps

4. Other means, to allow the balloon or balloons to be separated and stuck over again.

The balloon may be part of the construction of the wraps, to be ready for use. The advantage of temporary techniques is that they will allow balloons of different sizes and shapes to be utilized and even exchanged to match the needs of a patient, which may change and can be very much different than the other patients. Models of these wraps may be made having non-stretchable material combined with elastic materials. In such cases some parts of these units may be elastic while the other parts are non-stretchable.

An overview of the wraps may be made in the following ways:

To specify the make ups of the wraps or straps, the following itemization will be used, which also allows different modified units to be used easily for different uses as well.

1. The wrap/support unit will be made from a non-stretchable material that has the appropriate shape and size to be used in order to hold the balloon and provide the needed support. The ends of this unit will come around to attach to the ends of itself in some point of construction (the left or right side of the unit, its front, etc.) by different fastening means to make a complete circle.

2. The wraps will be made from a non-stretchable material similar to the model mentioned above in no 1 except this model is to have a clear (transparent) window for the observation of the area to notice any possible bleeding. This clear window may constitute or be made from a hard, clear, material of different shapes such as rectangles, circles, trapezoids, ovals, rhomboids, or any other shape as well to provide the needed support.

3. The wrap may be made from a clear (transparent) material that has the means of tolerating and maintaining the needed pressure. This wrap may have a soft inner lining/ cover to provide softness, comfort and prevention from contamination if the unit was not made to be disposable. The inner liner or cover may be attached to the wrap by different means.

4. The wrap may be made from clear (transparent) material of any form to have an inner lining permanently stuck to it to be part of its construction and provide softness and absorbency, as well as support. This lining will not cover the area of the window, to allow it to be clear (transparent). The other needed parts, such as adhesive areas or so, will also be clear.

5. The wrap may be connected to the balloon by a reversible or permanent means so that the unit will be ready for use.

6. The balloon may be incorporated into the wall of the wrap so that the unit will be ready for use.

7. A disposable inner liner may also be made to be utilized with different models of these wraps. Most commonly, the unit itself will be disposable.

8. The wrap may be made from elastic material, so that it can pull the balloon/bag toward the wound site.

9. The wrap may be made from combinations of elastic and non-stretchable materials, so that this combination will provide the needed support in front, with the pulling effect of elastic pulling the unit toward the wound site.

10. The wrap may be made to have signs, figures, measuring lines, configurations, shapes, signals and writing on its body or surface, in order to allow information, directions or similar communications of one sort or another to be done.

11. The shape of the wraps will be made to match the anatomy of the area in which they are going to be used, such as the groin, subclavian, wrist, antecubital, or chest areas, etc. Thus, the unit will match the area easily and fit comfortably and effectively to serve the purposes of use.

12. Importantly, the wraps may be made from combinations of separate pieces that may be connected to each other on a step-by-step basis for better use. Each of these separate pieces may have a piece of hard, clear plastic added to them permanently or temporarily. This can be of great help in certain cases; for example, in the construction of the unit for the groin it will be easy to have one piece for the upper thigh and another piece for the lower abdomen, so that at the time of use they can be connected to each other by different means. This process gives the advantage of first applying the upper thigh piece and preventing immediate bleeding, and then connecting the lower abdomen piece to secure the unit even more. Each piece may have a balloon or bag connected to it as well, to be functionally independent.

13. This unit may be made with a hard, clear, plastic piece held in place in its front, for example over the groin line (one part of it above the groin line in the lower abdomen and the lower part of it under the groin line and over the upper thigh area) and held in place by straps connected to its corners. The upper straps are to go around the waist area and the lower straps around the thigh area. The connection of the straps to the body of the support unit is to be totally versatile so they can be disconnected, re-attached easily and also twisted in different directions horizontally and vertically. This will make them easier to handle.

14. This support unit may be made with a hard, clear, front piece connected by straps to hold the unit in place securely. The shape of this front piece may vary depending to the shape and anatomy of the area. For example, the piece for the groin area will be chosen to stand on the lower abdomens upper thigh area. This hard piece may be chosen to cover only one part of the area and not the whole area. For example, in the groin area the piece for the upper thigh may be chosen to be hard while the piece for the lower abdomen may be made from a softer piece, to be more comfortable. Importantly, the connection point of the straps to the main body of the support unit may be made to be flexible, hinged, or snapped by one means or another to allow the rotation of these straps to occur freely, making a nicely maneuverable unit.

15. Some units may have a front wall with a clear door hinged to it, allowing the wound site to be checked or treated. In such models, the frame will be held securely by straps and wraps and the door will be hinged to the frame. An optional latch may hold the door closed.

16. The doors may have balloons attached or connected to them by different means, so that when the door opens, the balloon would also be easily moved away with the door as well. Then it can be placed over the wound again when the door closes.

17. The wraps may use pieces of hard, clear, supportive plastics placed on their front or rear sides of the balloons, giving more support and pressing the balloon. The connection between these pieces and the wraps may be permanent or temporary. The temporary means will allow these supportive plastics to be removed when desired.

18. The wraps may have clear windows covered by a piece of hard, clear, supportive plastic to be connected reversibly, so that they can be removed when desired.

19. The shape of the hard, clear piece may vary in each area to match the need. For example, in the groin area the unit may be made to have a clear, hard trapezoidal plate stand on the upper thigh area with an oblique line matching the groin line. The upper border of this unit is to be made from a soft piece for placement in the lower abdomen area. Overall, the hard trapezoidal piece can be placed and wrapped first to stand on the wound in the upper thigh area and then another strap is to be connected to the abdominal piece to hold the unit more securely and protectively in place. The job of the lower abdominal piece is two fold: first to press the lower abdomen area if needed, and second to hold the whole unit in place securely.

20. These support units are to have curves, softer edges, special shapes, etc., to make them the most comfortable units under the circumstances. The pieces may be chosen to be small; for example, the wide parts of the wraps may be diminished to be straps and the straps can be very thin and changed to be bands, etc.

21. The wraps may be made to match the shape and curvature of the body in the wound area, causing the least discomfort.

22. The connection of the straps to the hard body of the unit may be done by any possible means.

23. The wrap may have an open window in front of the wound site in order to use a clear balloon under and to allow vision to occur. This window may have a strong screen to hold the balloon in place.

24. Some models of the support systems may be modified properly to support a screw/lever plate system for pressing the balloon or bag on the wound site. In this case, the hard, clear part of the support system will hold the nut means of the screw to allow the screw to be turned forward and press the other plate against the wound. In some cases, applying pressure using a hard plate and a screw or lever will be enough to prevent bleeding. In such cases, the front plate will be made hard, clear and properly-shaped as well (this piece may be referred to as the wound plate). This piece will be exchangeable, having different sizes and shapes to allow a proper size and shape to be used for the area. It will have a connection place in its center to allow the tip of the screw or lever to be used properly. A tilting function will be used in this spot to allow the wound plate to stand on the wound area properly. Since in some cases (such as in the groin area) the plane of the wound area is not horizontal and has some angulation with the horizontal plane so the wound plate needs to be tilted. The pressure to the wound in such cases can be measured by having a flat air or fluid-filled balloon incorporated in the front or rear side of the wound plate, this balloon is to be connected to a proper gauge to allow the pressure to be known and decided.

25. The support system for the screw/lever plate system can be modified so that only the levers will be used to press the hard, clear plate to the wound site. So that in this case the hard, clear part of the support system will support the lever and press the other plate against the wound.

26. A modified model of the support systems mentioned for the screw/lever plate system may be used to support a hydraulic unit in order to press a hard plate forward onto the wound area.

27. Also, very importantly, the wrap or support system may be integrated with a pair of shorts or a similar shape to allow the patients to be mobilized comfortably while the pressure to the wound area is constantly applied.

28. The support units may also utilize a supportive unit for the back which has a tunnel to allow the strap or wrap to go through it freely without much resistance. This tunnel will not be compressed under the pressure of the body of patient and will have a proper size to allow the free motion of the strap or wrap inside it. This is to eliminate the need of the patient moving for the positioning of the wrap when the patient is tired, in pain or uncomfortable. Since this unit may be used on the X-ray table, then this unit is to be X-ray transparent.

29. The back support, mentioned in the previous no 28, may also be made to have an inflatable balloon or sponge with a flat rear surface that has the tunnel incorporated in it to allow the back of the patient to be supported as well. This unit is to be X-ray transparent as well and is to be placed under the back of the patients on the table to give comfort to the patient.

This unit may also carry a fluid of different temperature to provide warmth to the back for relaxing the back muscles. The warm temperature may be provided by the circulation of warm water or an electric heater.

30. Importantly, these wraps or support units may use a piece or several pieces of hard plastics to be temporarily or permanently connected to them, functioning as an immobilizer of the adjacent joint or joints if this needs to be done during this procedure.

31. Importantly, some parts of these wraps may be made to be harder or thicker than the other parts. Therefore, the thickness of the wall of this unit may vary in its length and area.

32. Importantly, the connection point of the straps to the main body of the support unit may be made to be flexible, hinged, or snapped by one means or another to allow the rotation of these straps to occur freely, making a nicely maneuverable unit, which can be detached if needed.

33. The flat, hard clear plastic part may be made to have a shape that can retract or expand. It can be made from two or more pieces that will slide inside each other, or one can fold over the other, be attached, screwed, etc., using one means or another to reach this goal. This is to allow its size and shape to be changed during use as simply as possible when needed.

34. The color, length, size of different parts, texture of materials and other characteristics of these units may all vary as well. It may be made clear in one part or another especially to allow the inspection of the procedure site, as well as the window in that site.

35. These units may have different coloring, signs, signals, lines, configurations, writings and other means of teaching and communication as well.

36. The connection of the straps to the body of the support unit (whether it is non-stretchable or hard plastic) is to be totally versatile so that they could be disconnected and re-attached easily and also twisted in different directions horizontally or vertically as well. This will make them easier to handle and more comfortable. Snaps, buttons, buckles, Velcro (TM) patches or any other possible connection means may also be used for this purpose.

The Bubbles, Balloons And Bags

Basically, the bubbles or balloons are for the creation or maintenance of pressure in the wound area to overcome the inner pressure of the vessel (an artery or vein and some part of the surrounding tissues of these vessels) to prevent bleeding and its related complications. Please notice that in this context the term "balloons" will be used to also indicate bubbles, since in the applicant's view, bubbles are functionally mini-balloons.

The use of air filled balloons. The units for the prevention of bleeding will use balloons or bags for the production and implication of pressure. Similar to the D. Device, the units mentioned in this application may utilize air-filled balloons for the generation and application of pressure. In such cases the balloons will expand with air to compress the wound area. This will be very useful, especially since the shape of the balloons can be changed and modified. Also, the pressure inside the balloons can be measured and controlled. The balloons may be made from polymers such as vinyl, latex, rubber or any similar materials. However, making them from a clear material such as vinyl is strongly expressed in this application, to allow vision in the wound area. The balloons in many cases will be pre-designed and shaped to match the shape of the area and fit the place well. For reasons that will be explained later there is a need for balloons with different shapes and configurations, and for this reason the general shape of these balloons may be circular, oval, triangular, square, rectangular, rhomboid, irregular, doughnut-shaped, ring-shaped with an opening to allow the unit to go around a sheath, etc. There may also be units with many openings, units with differently-sized openings in one unit, units with different thickness in their courses or any of their combinations which can be of help in a patient with special needs. These balloons or bags may be connected to a measuring device of different kinds to allow the pressure inside them to be known. They may be pre-inflated or inflatable.

The shapes of most of the balloons may be grouped as follows:

1. A flat clear balloon to be used over many places, such as over regular wounds, etc.

2. A balloon to have a special shape to match the shape of the area; for example, the groin unit may have a vertex in front to fill the groin line and allow pressure to the lower abdomen and upper groin.

3. A flat balloon with a soft front wall to assume the shape of the area.

4. A flat balloon in the shape of a ring or doughnut to go over a wound that needs to be dressed or has a catheter or sheath inside it and does not allow the regular balloon to be utilized.

5. A flat balloon in the shape of a horse shoe or a circle with one open side to allow it to go around a sheath or tube that is connected to the wound and would not allow a ring-shaped balloon to go over it.

6. A softer balloon such as a sausage-shaped balloon to go over areas which the wound would not allow other balloons to be placed around. Such cases occur after angioplasty, when the sheaths are in.

7. Different balloons may be needed to be shaped differently for special places, sizes and shapes.

The balloons may have different sizes as well, from small bubbles to big balloons. A very large balloon may be used in controlling internal bleeding. The thickness (the overall thickness of the balloon when inflated) may vary throughout as well, they may be thick in the center or some other point or may have almost the same thickness throughout. The thickness of their walls may vary from unit to unit to match the needs of the area, since some units and areas need more pressure than the others, while some may need very little pressure. Importantly, the thickness and consistency of the wall of a given balloon may differ from one area to another of the same balloon. For example a unit may have a thicker and harder rear surface than its front wall. Also, importantly, the balloon may have a hard area in its front to cause selective pressure to one particular area. For example, in the groin area, the balloon may have a hard, flat, rectangular area of about 6–7 by 7–8 cm or so with rounded edges in order to provide a solid flat pressure to the wound area and cover a rather large area. Importantly, although numbers are mentioned here, the applicant is specifically avoiding to give specific or fixed numbers regarding the ultimate size of these pieces. To understand his reasoning, he invites the examiner to notice the following discussion.

Some Discussion About The Shape And Characteristics Of The Balloons

Here the inventor wishes to give his opinion about the need for differently sized and shaped balloons, and why he recommends a very large selection of balloons. The inventor admits that he is avoiding to give specific fixed numbers regarding the sizes of these units. His reason for such an action is not to be ambiguous, but the fact is that size is relative. Take the case of a new born baby being catheterized for a possible congenital heart disease. In this case, an area of a half inch diameter in his/her groin is a large area compared to a large 260 pound, 6-foot-1 person. This is why the applicant believes that a balloon with one particular size is not a scientifically right answer for a group of non-homogeneous patients.

Also, please notice that the reason for having options for different balloons is that people, their weight, size, height, configuration, fat deposits, etc., are all different. The extent and nature of the procedures and conditions of patients are different as well. Some patients have simple diagnostic catheterization of the left region of the heart only, while the others may have a catheterization of the right and left regions of the heart together, an angioplasty of coronaries, the insertion of intra-aortic balloon pumps, etc. The number of the pokes in the groin may be different as well. Due to the patients condition, the experience of the operator makes a big difference. Naturally, a new trainee will probably need to take many more pokes in the artery and veins to enter the vessel. The coagulation status of the patients is important as well since the use of strong thrombolytic agents (which prevent from blood clot formation) will make patients more susceptible to bleeding. The length and complexity of the procedures will affect the patient as well: simple procedures will cause less vascular complications than prolonged, complicated ones. The condition of the wound at the end of the procedure, such as the need for keeping the sheaths inside the vessel, is one example of the important variables which have important impact on choosing the shape and size of the balloon. And after all, bleeding, in all of these conditions, needs to be controlled.

The more ill the patient, the more important the need is for the prevention of damage. The prevention of blood loss in a patient who has had a heart attack and coronary angioplasty is more important than bleeding in a normal person. This issue gets even more complicated if on top of these, the patient has an intra-aortic balloon pump inserted and has received potent blood thinners as well. So this issue turns out to be much more important than a healthy patient who is bleeding after a procedure. A reaction to a blood transfusion in a sick patient will be much more dangerous and even harder to handle than in an otherwise healthy person. This is the important area in which this inventor wishes to do something: "helping the sick complicated patient and preventing him or her from bleeding" and for this purpose he wants to provide an armamentarium of different sets of balloons, so at least one of them will fit the area and be functional. For example, one can go around the arterial/venous sheaths and the opening of a vessel for the intra-aortic balloon pump and be held in place by a proper wrap to protect the area. The inventor wishes to take part in helping the most difficult, hard to handle cases and prevent inappropriate human loss, pain, expense and complication.

For the case of bleeding around the sheaths, the inventor introduces balloons in the shape of rings or a similar shape which may have an open area in the periphery. For the opening around the intra-aortic balloon catheters, the same kind of balloons may be used as well. A sausage-shaped or flat balloon with a softer front surface is suggested to be utilized in these cases as well, to be pressed against the wound and fill the space. The consistency of the wall of these balloons may vary significantly to allow the final needed shape to be achieved.

The inventor wishes to express another important subject as well, indicating that importantly, the goal should not be to compress the surface opening of the wound on the skin alone but more to compress the openings of the arterial and venous walls themselves. The tissue where the needle and dilators perforate and damage during penetration and travel from the skin into the vessels and the surrounding tissue is the real target. This is not only to prevent the blood from leaking outside but also to prevent the blood from leaking inside the surrounding tissues, due to pressure. For this reason, he suggests providing a solid block pressure to the area with a hard, clear, flat plate (referred to as a "wound plate"), to compress the wound area. The shape of these plates may also vary, from triangular to square, circular, oval, rhomboid, trapezoid, irregular, etc. In some cases or models the wound area may be compressed by applying pressure with the wound plates alone, which can be achieved by the following means:

a. The use of inflated balloons, as mentioned above.

b. The use of a screw/lever plate system which has been mentioned earlier.

c. The use of a hydraulics system. In this case, a hydraulic unit will be secured on the front of the wrap to press a wound plate onto the wound area. This will consist of a piston (which moves inside a cylinder) and the free end of the piston outside (which will be properly positioned and placed on the center of a wound plate). The cylinder will be properly fixed on the hard part of the wrap, over the wound, so that by increasing the pressure inside the cylinder or by injecting air or fluid, the piston will be pushed against the wound. The cylinder will have a tube connected to another unit as simple as a syringe to allow the injection of the fluid or air inside the cylinder to create pressure. This unit may also be connected to a measuring device as well.

d. Any other proper means of pressing a wound plate, pre-inflated balloon or bag may also be used to perform this job.

Importantly, the balloons or bags will be made transparent to allow the visualization of the underlying wound. Importantly, the balloons, bags and wound plates may have signs, signals, printed lines, shapes and configurations of any kind to provide information and facilitate their placement and use. The color of one area, part or surface may also vary from one to the other in order to provide a means of transforming information to the users. Importantly, a balloon may be caged inside a proper cover in order to give a particular shape after inflation.

These balloons will be made from a clear polymer such as vinyl, plastic, latex, rubber or any similar material. They will be designed to tolerate higher pressure. The balloons may have the general shape of a flat rectangle, as in FIGS. 5 & 6, or with the shape and size to fit the anatomy of the wound area. These balloons will have one tube or more to allow inflation to occur as well as the pressure to be monitored easily. In some cases these balloons may be chosen to be filled with liquid; two tubes may be used to allow this to be done easily. The end piece of these tubes may have the shape of a male or female standard IV tubing ending to allow the easy connection of three-way-stopcocks or inflation units. The tubes may be chosen to be made from clear plastic or rubber and may have any functional appropriate size. The end of the tube or tubes may be temporarily or permanently connected to a three-way-stopcock or valve.

To summarize, the balloons may have the following characteristics:

1. The balloons may be filled with air, either to be inflatable, pre-inflated or permanently inflated.

2. The balloons may be filled with a fluid/liquid.

3. The balloons may have a combination of inflatable balloons and fluid-filled balloons to allow the creation, adjustment and measurement of pressure. In such cases, a flat inflatable balloon will be placed adjacent to a fluid-filled balloon so that the inflation of the air-filled balloon will compress the fluid-filled balloon toward the wound. A proper gauge may be connected to one of these balloons to allow the measurement of pressure to be done.

4. The balloons are to be made from a clear polymer such as clear vinyl, rubber, latex or similar materials.

5. The balloons may have pre-designed shapes to match the shape of the wound area, such as subclavian, wrist, forearm, groin, etc.

6. The general shape of the balloons may be circular, oval, triangular, square, rectangular, rhomboid, irregular, their combinations or any other shapes.

7. The balloons may have different sizes ranging from small bubbles for adhesive strips to large balloons.

8. The thickness (the overall thickness of the balloons when inflated) may vary throughout as well; they may be flat or thick in the center or may have almost the same thickness throughout.

9. The thickness of the walls of the balloons may vary as well. This is the thickness of the walls from which the balloon is made. Some units and areas need more pressure than others while some may need very little pressure.

10. Importantly, the thickness and consistency of the wall of a given balloon may differ from one area to another. For example, a unit may have a thicker and harder rear surface than its front wall, etc.

11. Importantly, the balloons may have a pre-shaped, hard, clear piece in their front, such a hard, flat, rectangular, clear piece of any size and shape such as a triangle, square, circle, oval, rhombus, trapezoid, etc.

12. All these balloons or bags will be made transparent to allow easy visualization of the underlying wound area; however, they may also be made in different colors.

13. The surface of the balloons or bags may have signs, signals, printed lines, or shapes and configurations of any kind to provide information and facilitate their placement and use. The color of one area, part or surface may also vary from one to the other again in order to provide a means of transforming information to the users and facilitating use.

14. The balloons may be caged inside a cover with special desired shapes in order to assume the desired shape of the cover after inflation.

15. The balloons may have one or more tubes for inflation and also for monitoring pressure easily.

16. Importantly, the inflation tubes may go through a hole in the support unit to reach the surface for easy handling.

17. The balloons may be connected to an alarm to prevent over or under inflation.

18. The use of balloons or bags filled with liquid will give the option of the application of heat (or coldness) to the area.

19. The balloons may have a means of connection to the wrap or the support part by having an area of adhesive, Velcro (TM), snaps or any other means to allow the connection of the balloons to the inner surface of the cover to occur. This connection may be permanent or reversible. When a layer of adhesive is used, it may be protected by a plastic cover which will be removed at the time of use to expose the adhesive. A weak adhesive may be used to allow the relocation of the balloon as compared to the wrap to be done easily.

20. The balloons may be held in place with the use of straps connected to their sides, corners or covers.

21. Importantly, it should be mentioned that instead of one balloon, combinations of balloons may be used to serve this purpose. So that one area may be pressurized while the other area would not, or one area can be covered by another balloon when one is not enough. This technique will allow a time and pressure difference between inflation as well. This is important in certain cases such as in groin units to allow the arterial and venous sheaths to be removed under lesser pressure.

22. Also, one balloon may be made to have compartments of its own or be made from a series of balloons in any form separate or combined inside one cover. These balloons may have a common inflation port or may have different inflation ports. Some of these balloons may be chosen to be pre-inflated. Alternative inflation of these balloons may be done and can be useful in some cases. Also, selective inflation of such balloons may be used in certain occasions.

23. Importantly, these balloons may be made to have hard, clear, plastic pieces of any shape to be stuck, glued or attached to their front surface in order to allow the shape of their imprint in the wound site to be modified in a desired and useful way.

24. The balloons may be pressed against the wound by any possible means: mechanical, hydraulic, etc.

25. These balloons may be made to be very large with many compartments and inflation ports for rapid inflation in special uses, such as the protection of Intra-abdominal aneurysms or in internal bleeding, such as the rupture of tubal pregnancy or similar conditions.

The Inflation System And Method

The inflation of the balloons may be done by:

I. A commonly used inflation bulb which will allow for inflation.

II. By connection of the balloon to a pressurized air tank of different sizes, with safety means to prevent overinflation and other complications.

III. Special syringes may be utilized as well to inflate the balloons. The syringes may be easily used with three-way-stopcocks. Also, syringes with comfortable handles which are connected to a gauge may be used as well. The syringes will be useful in the injection of liquids inside the balloons or bags. The fluids can be suctioned from the IV bags with the use of a three-way-stopcock to inject into the balloons or bags. Commonly-used syringes may also be used effectively.

The inflation tubes can be made with different sizes or colors. A conventional IV tubing with a male end to match and fit the end of the inflation port may be used as well. A three-way-stopcock will be utilized to allow the closure of the air or fluid flow as well as the means of connection to a tube connected to a gauge for the purpose of monitoring the pressure inside the balloon. An alarm system may be used to inform of over or under pressurization. Safety valves may also be incorporated to serve this purpose. When pressurized tanks are used, then a control system and safety valves will be incorporated in the system to prevent the pressure from exceeding a certain pre-determined ceiling.

Figure 24:
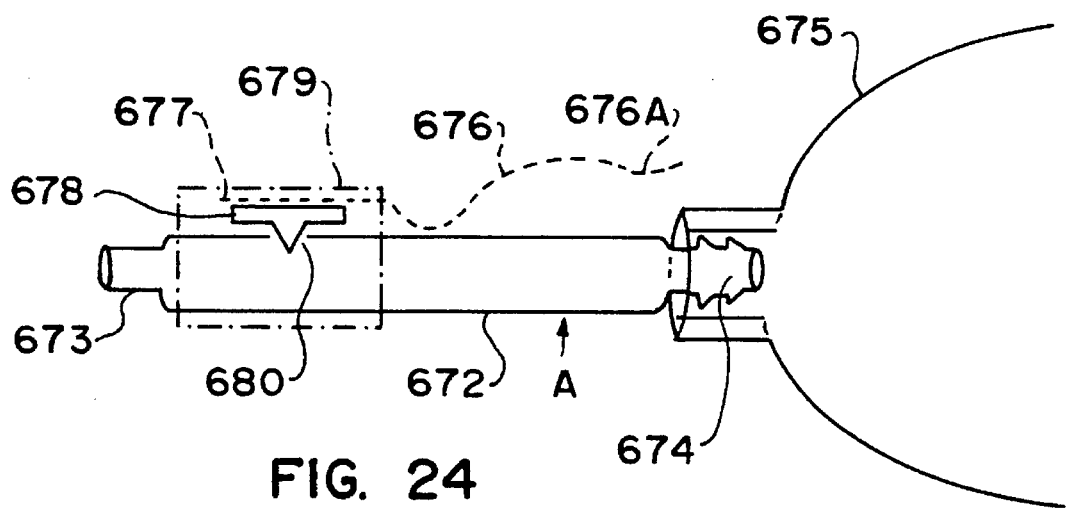
Figure 25:
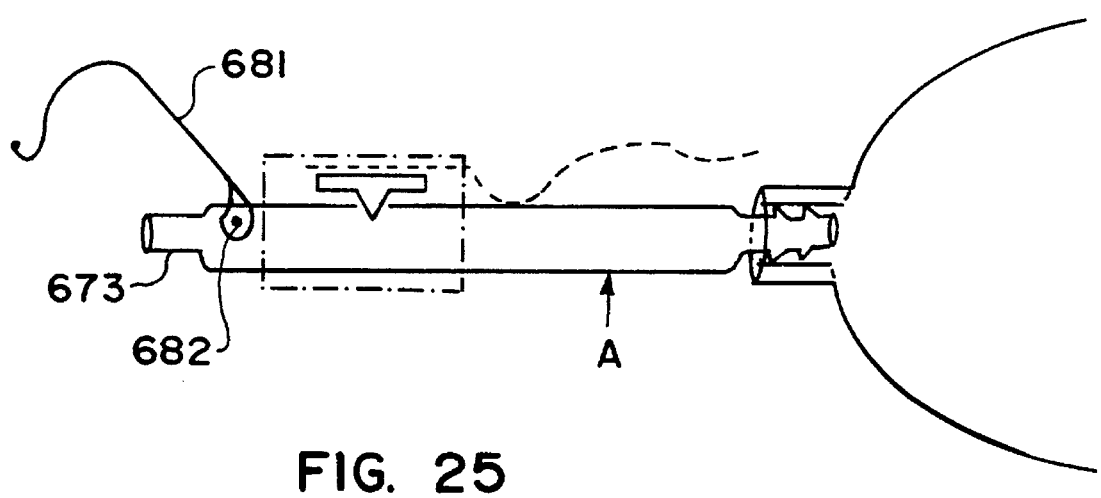
Figure 26:
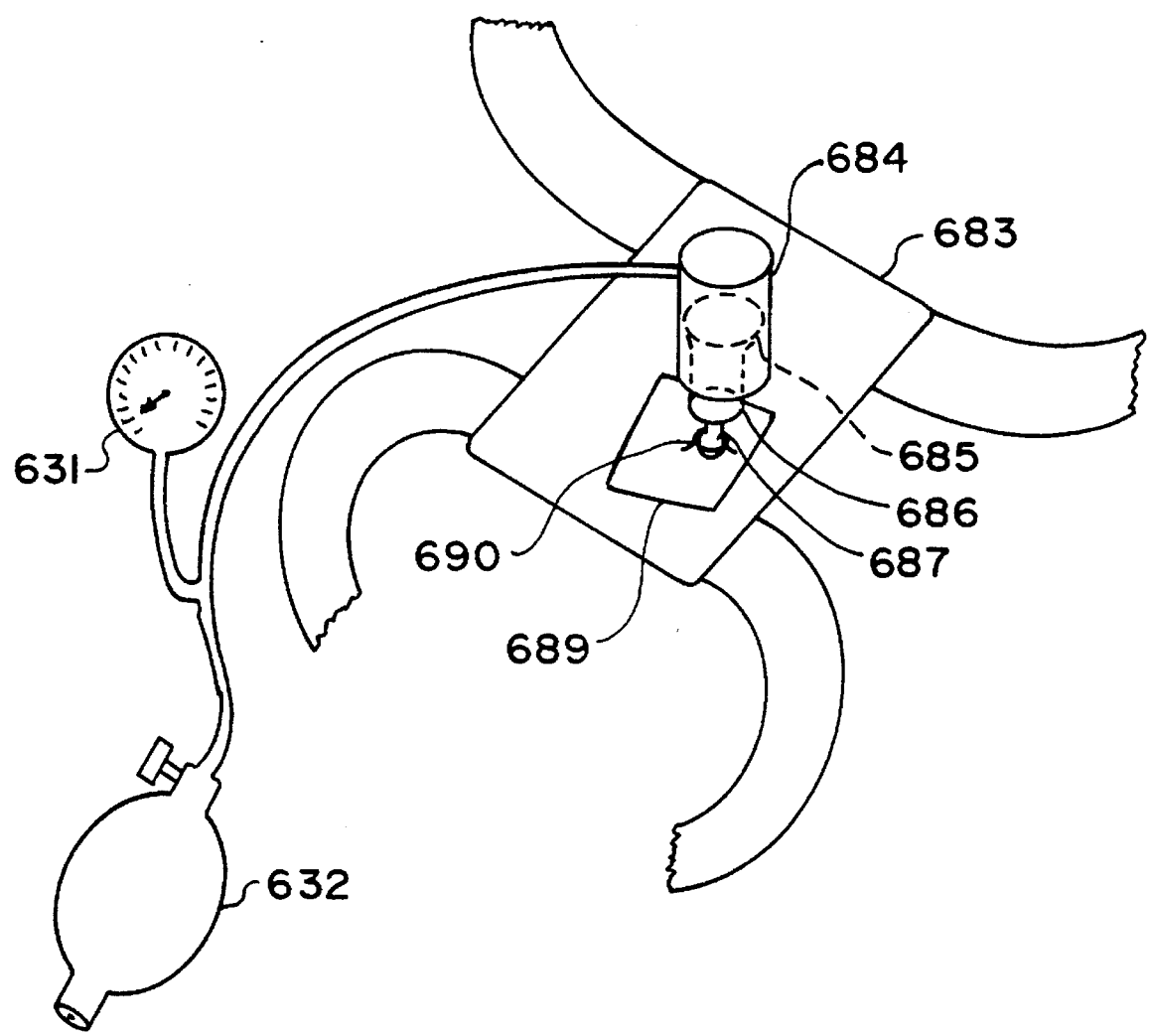
Figure 27:
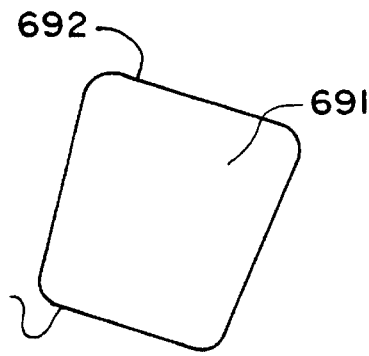
FIG. 27 shows a hard clear trapezoid plastic piece that is to be placed on the wound site under the balloon in order to provide a flat pressure on the wound site. The shape and size of this unit will vary.
Figure 28:
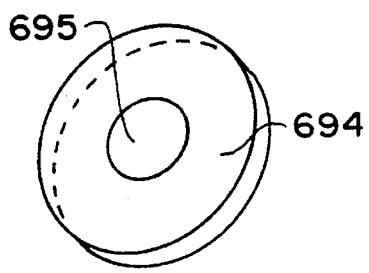
FIG. 28 shows a doughnut-shaped balloon which is made to go around a unit and be placed on the wound.
Figure 29:
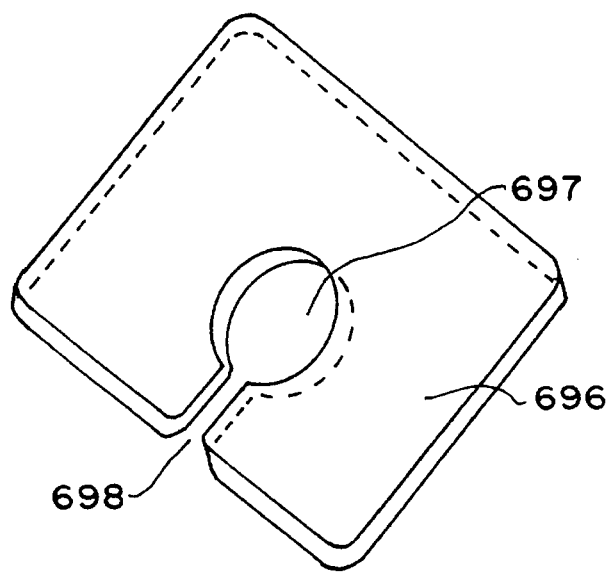
FIG. 29 shows a differently shaped balloon in the shape of a rectangle that has an open center connected to an edge via a slot. This is to allow the unit to go around an inserted piece such as an intra-vascular sheath connected to a tubing or similar units and be placed on the wound.

Automatic shut downs may be incorporated into these methods as well. Importantly, one particular model of inflation bulb will be made to allow it to be covered by a disposable clear plastic for the prevention of contamination. This model is changed to avoid the use of rotation for the control of the air flow, and for this reason a model will be used with a knob to release the air. One sample of such a unit is shown in FIGS. 24 & 25. In this unit pressing a button 676A will cause the release of air and a one-way valve, placed in spot A, will prevent the air from returning to the bulb or escaping. Many other models may be made to prevent the need to use a rotational knob for controlling air flow and allowing the unit to be covered by a disposable cover. The tip of these units may also have a means of secure connection to the other pieces (as shown at no 681 in FIG. 25). This is a C-shaped spring that is connected to the end of a three-way-stopcock and will go over the other end of the tubing. This spring will hold these two ends together securely, preventing them from being disconnected by accident.

Importantly, in other models, a C-shaped spring with openings on its ends (as shown in FIGS. 18 to 22) may go from one end of the tubing or three-way-stopcock over the end of the other tube to hold these two ends together securely and prevent accidental disconnection. The FIGS. 23 and 23A show how this C-shaped spring may be hinged to one end and rotated to go over the other side so that the mechanism is more simple. This unit and technique has many uses and may also be used in securing the IV lines for similar connections. Importantly, one other easy means of securing these tubes introduced here is to have the receiving or female end of these tubes have teeth or notches that will engage with a special circular notch (goes around the end) from the other end, as shown in FIGS. 38 & 39. By pushing the male end, the teeth or notches will move away and allow the tip of the male end to enter the opening from the other end and be held securely inside. It will not be pulled back unless the notch is released as mentioned in those figures. The model in FIG. 39 has a lever while the model shown in 38 needs to have the tip of the notch pulled away for release. The notches may be made to be multiple in number in each connection sites. This method also can be used in securing the ends of the IV lines as well. The advantage again is to avoid rotational movement, which is believed to be hard for many older people.

B. The use of fluid or gel-filled balloons with the above mentioned wraps. In this model, instead of inflatable balloons, the unit will use a special pre-inflated balloon filled with air, water, fluid, liquid or gel to assume the shape of the area and transmit the pressure to the wound area. This bag may contain numbers of air-filled small plastic bubbles to function as a buffer, allowing the pressure to be reserved and dissipated later. These small bubbles will be held in proper position inside the bag by the use of a structure or screen, made from plastic, which was shown in the previous application. Importantly, the bags that contain such air or fluid may have their own inner compartments and walls to prevent shifting fluid as well as preventing all the unit from deflating if one of them was punctured. The air-filled balloons may also have such features. A fluid or gel-filled soft bag will have the potential of accepting and assuming the shape of the place on which it is placed; when the pressure is less, the unit will assume the shape of the area, and when the pressure is high, it will prevent change in the shape of the area. A hard or semi-hard piece of shaped plastic may be utilized and placed between the front wall of the bag and the surface of the wound, giving shape to the area.

Also, these bags or balloons may have an air-filled soft balloon connected to a tube. Alternately, this balloon may be in the shape of a dumbbell, one end of it inside the bag and another end outside to be utilized as a means of measuring the pressure inside those bags.

Importantly, these bags or balloons may have an open area in their centers in order to allow the inspection of the wound site. Thus, it would not be necessary to remove the whole unit to inspect the wound site all the time. A door may be connected to this so that it can be opened for direct inspection. The inner wall of the door may have a matching balloon to fit the area. These units all will be chosen to be transparent to allow the observation of the wound site.

The balloons mentioned above may be made in the shape of a flat, rectangular, circular or any other three-dimensional shape which will fit the anatomy of the area and serve the purpose. The function of increasing the pressure in the area may be achieved by:

a. Placing the fluid-filled bag on the wound site under the non-stretchable wrap and then pulling the wrap by hand or any other method and securing it (while being pulled) to increase the pressure in the area by squeezing the bag mentioned earlier against the skin.

b. Using an elastic wrap or strap. When the needed pressure does not need to be high (such as during venous bleeding), then a proper elastic wrap or strap may be used to be strong enough to pull the balloon or bag against the wound to keep it tightly in the needed area. This technique may be used with the shorts as well.

c. When there is a need for a higher pressure application (such as in arterial cases) then an inflatable balloon may be incorporated into the system and placed between the non-stretchable wrap (may have a hard transparent piece in it) and the rear surface of the bag (that can be separated by a hard plate). So that the inflation of the inflatable balloon would create pressure and press the first balloon against the wound site.

d. By incorporating a spring between the non-stretchable wrap and the base of the balloon to press against the balloon when it is held tightly by the non-stretchable wrap.

e. The pressure to the wound site may be applied by pressing the bags with the use of a hard, flat plate with a non-stretchable support and a screw/lever plate system. So that the hard, flat plate will be moved forward by the rotation of a screw as was shown in D. Device 4. This method will also help prevent changing the shape of the area and at times give special shape to the operated area as well.

Importantly, when the hard, flat plate is used with this system, the center of the plate will have a small (about one cm diameter) empty cradle (similar to half of an empty egg shell) to accept the matching round, global shaped tip of the screw to be situated inside it. This combination is to allow the hard plate to easily twist inside the cradle in many angulations, to allow the flat plate to sit on the wound site of the groin easily in an angular or oblique direction. This is due to the fact that in many cases the surface of the area of the wound is not in a flat and horizontal plane but the plane of it has some angulation with the horizontal plane.

In some models, instead of having the screw push the center of the hard plate, it may be connected to a frame that will divide the pressure to the corners of the hard plate in order to prevent the center of the unit from being obstructed for vision purposes.

f. By pressing a hard plate toward the balloon with a lever so that it will press the balloon onto the wound site.

g. By use of an air-filled balloon or combinations of balloons which are pre-inflated and will be placed and used on the wound area to act as a buffer, having their inner air squeezed by the pressure caused by pulling the non-stretchable wrap.

h. By the use of a series of bubbles that will be constructed and properly placed inside a fluid or gel-filled bag. These bubbles are to act as a buffer and are to hold pressure by having their inner air compressed by the pressure caused by the pulled non-stretchable wrap. These small balloons or bubbles will be held in place properly by a network or screen made from soft plastic for this purpose, to prevent them from wandering around inside the fluid.

i. Pressing a clear, flat, hard plate against the balloon or bags on the wound site by a spring system pulled by a non-stretchable wrap would also be an effective means of creating and maintaining pressure on the wound site.

j. By using a hydraulic system that will use the hydraulic mechanism to press the clear, hard plastic onto the wound site or onto the balloons or bags on the wound site.

k. Any other methods or possible means may also be utilized to serve this purpose as well.

These methods and means, when used appropriately, will create a force to press a pre-inflated balloon, fluid-filled bag or a properly made hard, clear plastic against the wound of the skin to serve the intended purpose.

Naturally, these units are always to be used after considering the circumstances of the patient. If higher levels of pressure are needed, then units that can produce higher levels of pressure are to be utilized. Similarly, low level pressures are to be used when the need for pressure is less (such as in venous cases and when the patient is stable and ready to be discharged from the hospital).

It is the belief of this inventor that these units will provide pressure to the tissue around the vessels and limit the chances of the expansion and dissipation of the blood or secretions into that area.

Importantly, the balloons or bags and their covers can all be made from transparent clear material to allow the wound area to be visualized well for possible bleeding. Optionally, a small battery-operated light bulb may be incorporated to allow the lighting of the wound area to occur for a better visualization. Also, a magnifying lens may be stuck to the cover to allow the wound site to be magnified and visualized well.

In some models the wrap may not have a clear window but instead an open window. However, in this case the open window may have a series of threads or bands of strong clear material going from one side to another, up and down, in screen fashion in order to hold the balloon under it sturdily. The combination of the open window and the clear balloon will give the opportunity for the observer to see the wound. Naturally, the size of the open window needs to be smaller than the balloon or the screen is to hold the balloon in place securely.

The front surface of the balloon or bag will face the wound area. Importantly, this surface may be made in different shapes and consistencies; in one model it will be made to be soft and pliable in order to easily fill and assume the shape of the area. In others it will be made to be hard to provide a shape for the protection and shielding of an area or some part. In some cases, the front surface of the balloon or bag may be covered by a gauze pad that may be chosen to be stuck to it. This gauze pad may have a plastic base to prevent bloody, wet or contaminated materials and secretions from going through. This gauze pad may have a film of adhesive on its rear surface to allow it to be stuck on the surface of the balloon/bag. Importantly, the special shape of this bag, when modified and made in different sizes, will give the important freedom of using it in different people with different body sizes as well as different shapes in the site of use. Importantly, the size, thickness, coloring, relative thickness of the walls, hardness, shape and other characteristics of these balloons may be different in different models in order to make the best unit for each area.

A properly-shaped spring may also be placed between the hard plate and the pre-inflated balloon/bag in order to allow the creation of pressure in the balloon/bag. This spring may have the shape of a cake to be caged inside a cover to allow it to be inserted easily or positioned in the rear side of the balloon/bag between the rear surface of the balloon/bag and the inner surface of the wrap. Importantly, the wrap in this case will be made non-stretchable, even though in some cases elastic wraps may be also used as well. The strength of these springs will vary to allow the exchange of these units to be done and more choices to be made.

Importantly, the bags or balloons may be connected to the wrap by having a small bubble of soft plastic which contains adhesive to be placed on the surface of the balloon so that when inflated the pressure would cause the adhesive to leak out and stick two sides together. This can also be made by having a layer of adhesive covered by a layer of plastic with weak points, that when squeezed, would cause the leakage of the adhesive in the weak of the areas between the balloon and wrap. This is a technique with many uses as well.

Importantly, the hard, clear plastic which makes up the front part of some models (FIG. 42 no 750) or is used in other models with the support unit, may have a hole in its front to allow the tubing of the balloon to go through it. This hole may be larger than the size of the tube to allow adjustment to be done, and may be circular, oval or similarly-shaped as well.

It should be mentioned that although these units are mostly shown for the right side, it is intended in practice to make models for each side (one model for the right side and a similar model for the left side).

The Use Of A Second Cuff

As it has been previously mentioned in D. Device 4, a second balloon or cuff may also be utilized for a better function. This application emphasizes the same technique in certain cases and also with different purposes as well in order to allow a differential or selective pressurization to be applied. One example was mentioned: utilization in the arm. In such cases, a unit will be used to inflate a cuff in the higher arm in order to prevent blood spillage from the open artery and allow better functioning in the lower area. In that case, one pressure cuff unit will be wrapped above the procedure site on the arm to function like a pressure cuff, stopping the circulation of the blood above the antecubital area so that this prevents bleeding from occurring during the short period of cleaning and wrapping and allowing a better dressing and related job. This piece may be connected removably to the main unit by a strap. In other cases, combinations of balloons will allow one area to be pressed differently, selectively and alternatively as well for better work.

Importantly, double balloons may be used in the groin area. One will stand over the sheath area above the opening of the skin in the abdomen side, and will be inflated while the sheaths are in place. Then the sheaths are to be pulled out and then the second balloon is to be inflated in order to cover the area of the wound on the skin. Both of these together are to make a very effective seal to prevent bleeding. Many other combinations are possible for intelligent uses.

The Advantages Of These Units, Methods And Means

In the opinion of the inventor these units will be of extreme value in the prevention of bleeding in the wound areas as well as in intervention sites and will be of great help in such patients. Some of these benefits may be mentioned as follows:

1. The use of smaller units will help in the prevention of bleeding after cuts and certain simple wounds, such as after phlebotomies and even after the injection of medication in anti-coagulated patients or similar conditions. The clear front will importantly allow the visualization of the wound site to be done. And the exchangeable clear balloons are of significant advantage:

2. They will be of significant help in taking care of wounds, importantly when made with clear windows, they will allow a better observation of wound areas and an early medical response.

3. The cases with elastic sleeves will be of great value in patients who may injure their hands and limbs. This will allow one hand to take care of the other hand or limb, which is very difficult to do when hand wounds occur. The units that allow the length of the unit to be altered after use have a great advantage.

4. The lighted units may be of special use in certain circumstances such as during battle or similar conditions at night, in the case of which the use of flash lights is not possible for one reason or another. One reason is the fact that holding a flash light many times needs a functioning hand.

5. These units or similar models will be of significant use after surgeries and similar conditions.

In the case of the prevention of bleeding after the cardiac catheterization and similar procedures, the following benefits are to be considered.

1. First, since in most of those models the pressure inside the balloons are easily adjustable, controllable, (unlike the commonly used sandbags) and are not gravity dependent, then they would not limit the patient to one position, which will dramatically help the comfort of the patient.

2. These units will practically eliminate the heavy use of adhesive tapes and chemicals, (such as Tin Co Bin), will help reduce the patient's pain and bad reaction due to the use of such materials, and will cut costs as well.

3. These units will allow patients to be mobilized sooner, be more active and even be discharged earlier when the bleeding gets under control. For example, when used in cases such as in the groin after cardiac catheterization, this system will allow the patient to sit earlier, stand and move earlier without being confined on the bed. Even the chances of bleeding after cough or vomiting will be less when the area is protected. In practice, many patients suffer from back pain and other problems and staying in bed is one of the last things in the world some of them want to do.

4. The fact that the balloon can be exchanged easily is of great value, allowing special and unique uses such as using balloons for delivering different temperatures to the area as well. Using a cold compress to prevent localized hematoma is a good example. This can be done by filling a special balloon with iced water and placing it on the wound area (or having a cold gel-filled unit kept in a cooler or refrigerator for this purpose) while still providing pressure as well. Even in later stages the warm compress may be applied by the same technique.

5. This unit, due to its inherent protection and safety, will allow the patient to be discharged earlier. This has many benefits for the patients as well as the medical staff. The fact that the patient can be sent home sooner prevents many people from driving long distances, especially in winter in dark and slippery roads, since not all outpatient (many of these procedures are now done on an outpatient basis in which the patient comes in the morning and goes home in the afternoon or night) cases start and finish in the morning. The fact is that the need for medical supervision will be much less, diminishing the cost of hospitalization and perhaps paying for this new unit many times over.

6. This unit also has its own value in preventing anxiety, apprehension and fear in the patients as well. It allows patients to cough, raise their head off the bed and even sit up much sooner without having the fear of causing damage to themselves. This unit or different models of it can be used and kept on the wound area without much discomfort for a longer period of time, even during transfer and after being discharged from the hospital. This is in order to provide many patients with much-needed physical and psychological security, and it will allow them to feel secure and comfortable (the protective shorts are specially designed for this purpose). This will cause patients to start their normal lives earlier and return to their jobs sooner.

Since bleeding will stop if the local pressure is higher than the blood pressure of the patient in that area, the patients can be educated in this regard to learn how to increase the local pressure by inflation of the balloons if bleeding occurs. So importantly, this unit provides a means that gives the patient a way of controlling bleeding, which increases their feeling of safety.

7. Most importantly, this unit is more effective, adjustable and controllable. It is the belief of the inventor that the use of such units may prevent from further damage to the walls of the vessels, such as the formation of pseudo-aneurysms and AV shunting in the wound site due to the prevention of blood leaking outside of the vascular lumen, which may be of extreme value. Also, the long term observation is to see whether the large bruises seen after cases of groin interventions would occur again. By advising the use of hard, clear plates and pressure to the areas of the wound, the inventor has hopes of preventing such complications.

8. It should also be considered that the ease of use and efficiency of such units will decrease the work of trained medical staff significantly, which is an important issue when the overall cost of medical care is to be considered.

9. Importantly, this unit, with only minimal modification can also be very useful in patients with inguinal hernias, after hernia operations and many other surgeries and related conditions as well.

The shape of the hard plastic: The front of some models of these units may be made from transparent plastic, which will stand in front of the wound site to be the backbone of the support unit. The shape, efficiency and importance of each piece will vary from one side to another. For example, in the groin models, it will have a piece to stand on the upper groin, lower abdomen area such as piece 639 in the FIG. 12, or no 613 FIG. 11. This unit will be held in place by straps or wraps, such as in FIG. 13, no 643 and 641. This hard piece may have a curvature to match the side of the procedure and the overall size and shape of this unit. For example, in the upper thigh area, the unit may have a mild curvature to match the curve of this area. It may also have an oblique side to fit the groin line. In this regard, again, the hard part may be made from two pieces that will be held next to each other or be hinged, so that when the patient sits down the unit will allow this to happen when the balloons are deflated or multiple balloons are used. Importantly, the hard pieces may also be temporarily placed or attached in the wall of support unit so they can be removed from it easily. Thus, when the patient needs to sit, the soft material will allow this to happen. In such cases the unit may have a soft, pliable plastic to allow bending to occur in the groin area.

Importantly, the hard, clear plastics which are used for making the front part of the support units or are to be used with them in the groin and upper thigh area may be made from combinations of pieces that will allow their size and shape to be changed easily by having one screwed, held or hinged to one another by other means. One model of these is shown in FIG. 41. In this case, one part can slide over another to allow the size and length of this unit to be controlled and changed easily. Any other possible means and methods may be used for this purpose as well.

After explaining the general background and idea behind such units, the applicant now wishes to mention how different models may be made and used in different areas of the body to do this very important job.

The Units For The Prevention Of Bleeding In Wounds And Small Areas

1. These will be made from a unit that has a clear center piece with a clear balloon which will be held in place by the use of bands or straps whose end pieces have a film of adhesives protected by a plastic cover that will be peeled off at the time of use. These units will be placed in the wound site and be used by having the ends stuck to the side of the area. In some models the balloons will be separate from the band part to allow a choice of balloons to be made. The balloon may be attached to the band or be placed under it at the time of use. For this purpose small, inflated, clear balloons will be placed on the wound site.

2. The units with a clear center and a clear balloon placed in the wall of an elastic strap or a sleeve which will go around the fingers, limb, or similar places. The presence of the clear front piece and the balloon or bubbles of these units is very important in allowing the visualization of the wound site to occur. The outer surface of these units may be made to accept a non-stretchable tape to control its length.

Elbow Unit

Please notice FIGS. 1, 2, 3, 7, 10, 11, and 14 from D. Device 4.

The background: In general, cardiac catheterization, coronary angioplasty and related interventions are commonly performed via the vessels in the groin area. However, in certain centers, these procedures may be done via antecubital area especially in some patients with severe obstruction or occlusion of the femoral arteries or their distal aorta as well as cases such as Coarctation of Aorta, in which the upper portion and arch of the Aorta can not be reached via the groin method, in which the artery in the arm needs to be intervened. In such cases the brachial artery in the antecubital area of the patients would be invaded and a large core needle will be entered inside the inner lumen of the artery by perforating the front wall of this vessel. A dilator will be utilized to make the hole larger for the insertion of the sheaths and catheters. After the termination of the procedure the hole and the area would need to be dressed and the bleeding prevented. This is commonly done by heavy dressing of the area by gauze, bandaging, and adhesive tapes; however, this method is not best, does not give the best pressure, and is not adjustable as well. The pressure can not be measured, controlled, increased, or decreased. The use of adhesive is problematic due to its related skin reaction and pulling hair at the time of removal. The direct inspection of the wound is not possible without removing the dressing, and changing dressing is not simple at all, etc. Therefore, the method specified earlier in this application is recommended to be utilized here again to control the bleeding in this area after such procedures. This was introduced in the inventor's previous application of D. Device 4, (please notice that the figures and numbers in this part are from D. Device 4) in which a non-stretchable wrap (FIGS. 1 & 2, no. 1) which matches and fits the anatomy of the antecubital area will be utilized comfortably, however not allow the joint to bend. They may be like a layer of molded hard material that fits the sides of the elbow joint and will be placed or attached in the sides of this unit by a means of temporary fastening. This method will allow them to be connected temporarily and removed selectively after use. This wrap will be made to match the shape of the area. The borders of this wrap such as the upper border no 3 FIG. 1 and lower border no 4 may have a rim or extensions going up and down on the arm to make a technique to secure the placement of the balloon in place. These rims may be made thicker, stronger and more pronounced than the wrap to function as a shallow wall and to hold the balloon inside. They may have one or bands of elastic or stronger material for better security and control of the inflated balloon.

This wrap may be made from a non-stretchable material, as well as clear vinyl, latex, a polymer or any other suitable and appropriate materials or their combinations.

Importantly, this wrap will have a clear (transparent) window (no 14 FIG. 3) to allow the underlying part and area to be visualized; this is especially useful for observing the potential bleeding. This window may be made from a soft plastic or a hard clear plastic to provide rigidity and support as well (also to prevent the joint from bending). This hard, clear plastic may be placed reversibly to be removed when desired. A combination of materials may be used as well. For example, the inner part of the wrap may be made from a comfortable, soft, fluffy, fabric which will be connected to the outer protective layer. The clear front part will not be covered by this soft layer so that it will not block the view.

Importantly, in some models this unit may also have a door-like window to allow observation and wound care to be done without a need to dismantle the whole unit. The sizes, colors, relative sizes, thickness, shapes, consistency and all other characteristics of these units and their parts may vary to allow different units to be made to fit different people and different needs. A unit made from latex or similar material will allow sticking a non-stretchable adhesive tape on the outer surface of the unit to make the unit less stretchable and more tight (this technique was explained in D. Device 3). This will decrease or eliminate the need for the patient's skin to be taped by adhesives. A durable material may be used for the construction of these units as well as disposable ones.

Figure 8:
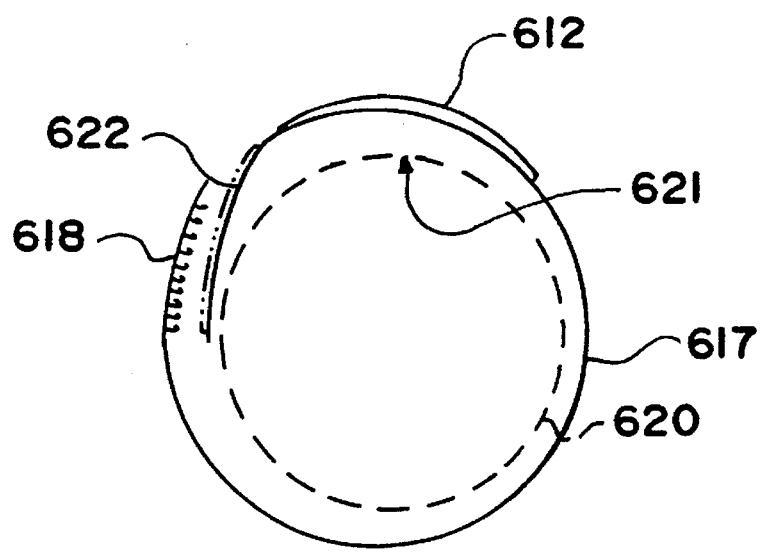
Figure 9:
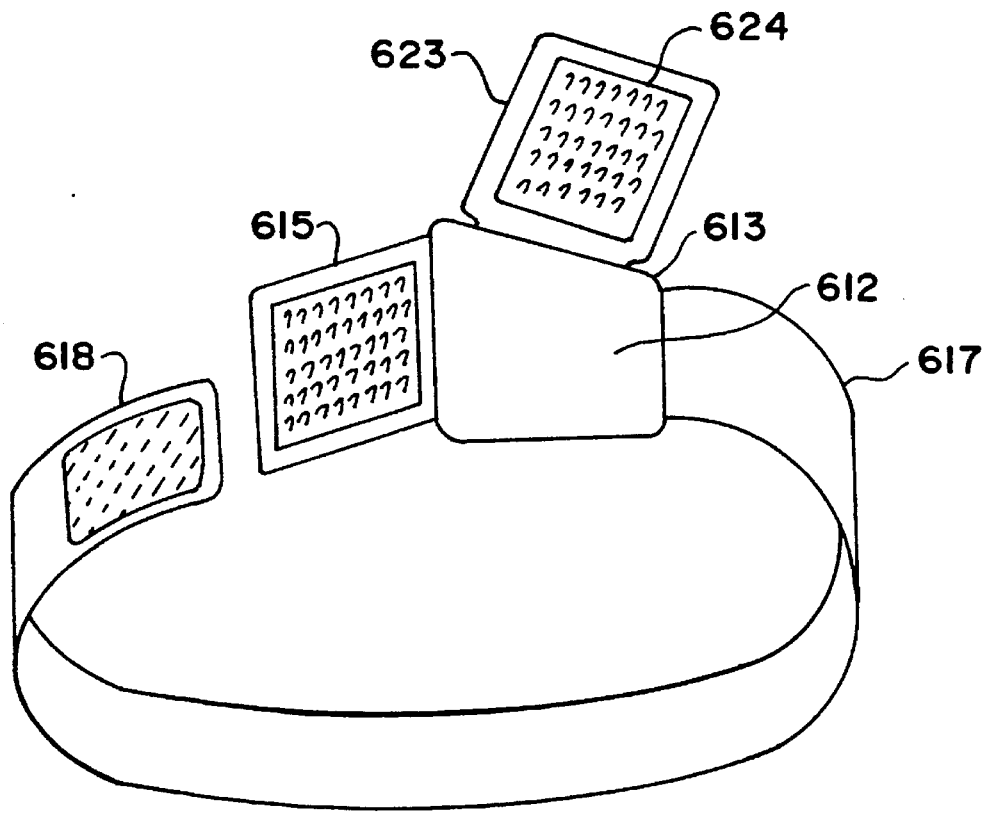
Figure 10:
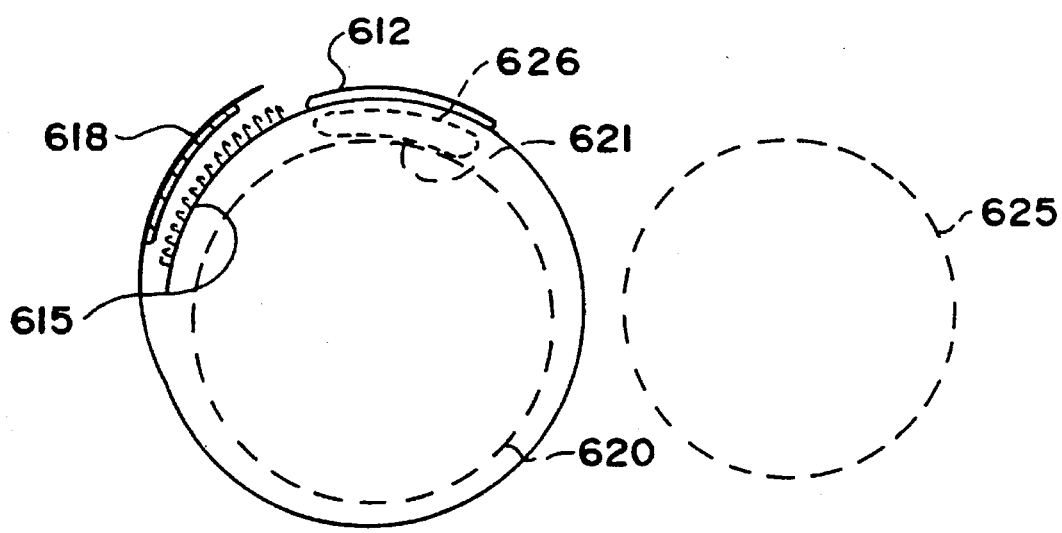
Figure 11:
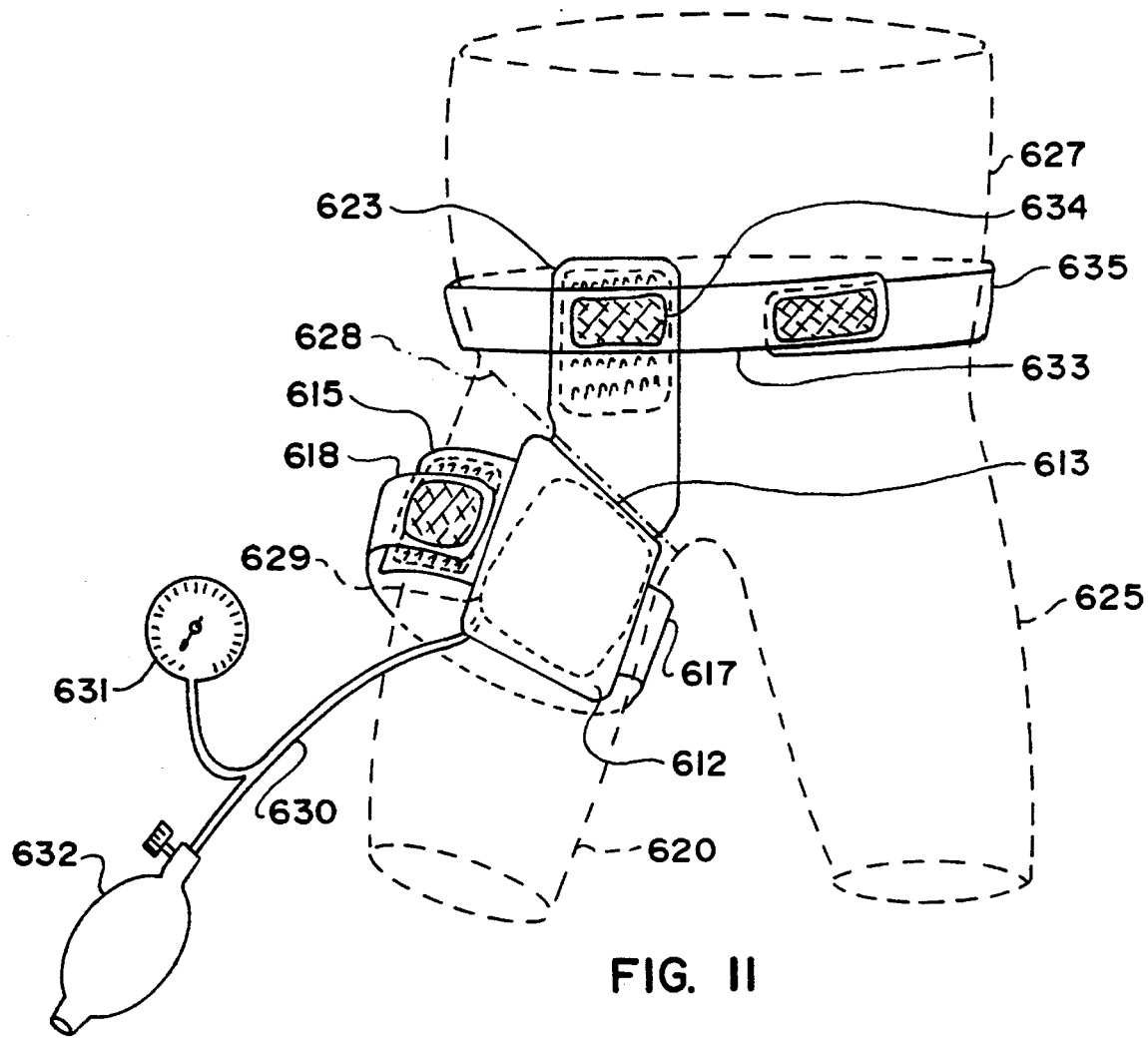
Figure 12:
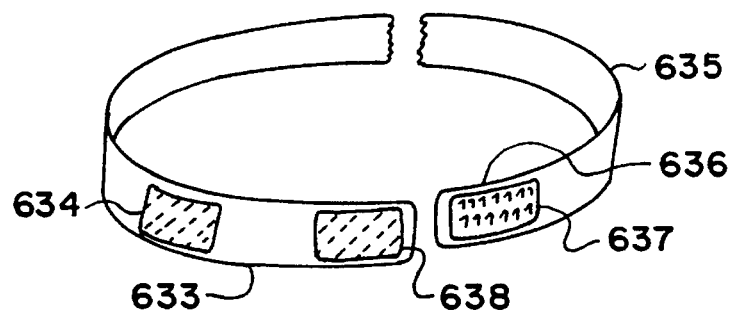
Figure 13:
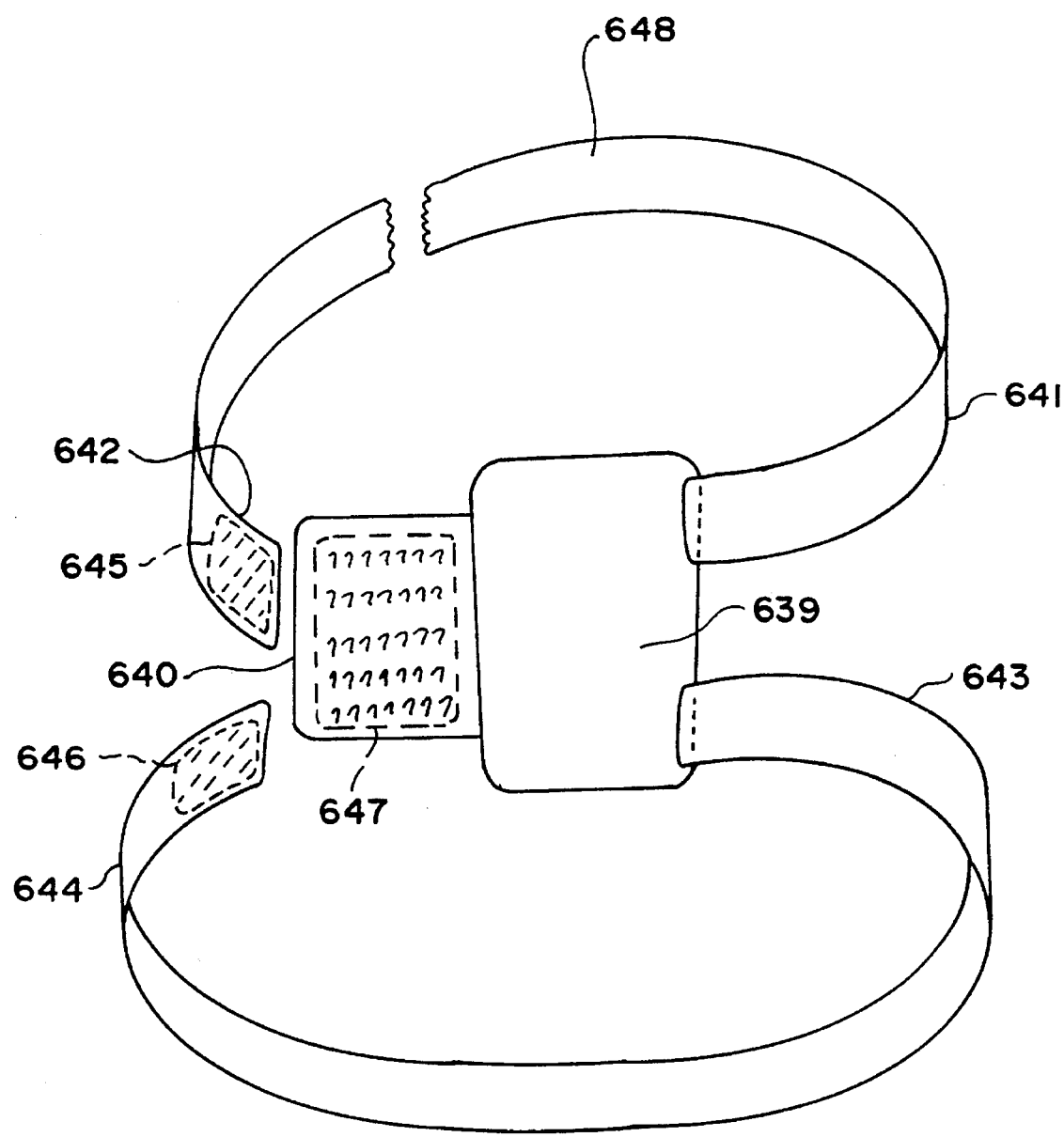

The balloons (please notice FIGS. 5 and 6) will be made from clear (transparent) materials to allow the inspection of the area to occur easily. It will have an inflation port no 28 to allow the creation and maintenance of pressure to occur in this area to overcome the inner pressure of the artery and prevent bleeding and its related complications. It may have a hard rear wall no 37 (please notice FIGS. 8 & 9) with a softer front wall no 38. It may also be chosen to be a pre-inflated balloon or bag filled with air, fluid, or gel (FIGS. 12 & 13). FIGS. 10 & 11 show how such a pre-inflated balloon/bag no 45 may be placed on the wound site 19 and be kept inside the supportive wrap no 50. The pressure on the wound may be done by using a screw/lever model, such as the one shown in FIGS. 10 & 11.

The balloon and wraps may be connected to each other temporarily or permanently. Also, a second balloon or cuff may be utilized with this unit as was explained in the text. This second balloon will be made to be properly shaped with a balloon placed inside a non-stretchable cover with proper curvature to be placed in the mid to upper arm area. This unit is to block the circulation of the blood to the lower arm when inflated, in order to allow the needed work such as cleaning and wrapping, etc., to be done easily with lesser blood spillage. This piece may be connected removably to the main unit by a strap.

Importantly, one model will be a modified version of the above mentioned unit and concept to hold and support the sheaths in the antecubital area when angioplasty or a similar procedure is done in this area. To prevent the sheaths from having unwanted movement when they are to be kept in place for a longer period of time after coronary angioplasty. In such a case, the unit will have pieces of clear, rigid parts and pieces in its construction around the wound or the sides to prevent the elbow joint from bending. A cradle may be attached to the outer surface of this unit to hold the sheath in place securely. This will use the same idea and principles that the applicant has introduced for the groin in his application of Special wraps and dilators and Foley catheters to the PTO. In such a case, a non-stretchable wrap will go around the elbow joint and will have an opening in its front to allow the sheaths to go through it. Importantly, a flat, clear balloon with or without a hole in its center or combinations of differently shaped balloons may be utilized to make up the means of pressing the wound area and prevent bleeding around the sheath and in the wound site. The front part of this unit will be made clear to allow observation of the wound site. The end pieces of the wraps may be connected by pieces of Velcro (TM) or similar means.

Figure 21:
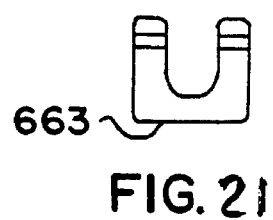
Figure 22:
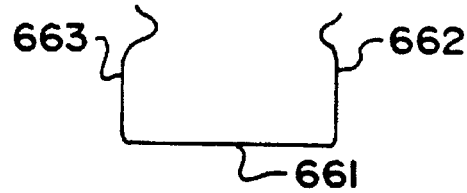
Figure 23:
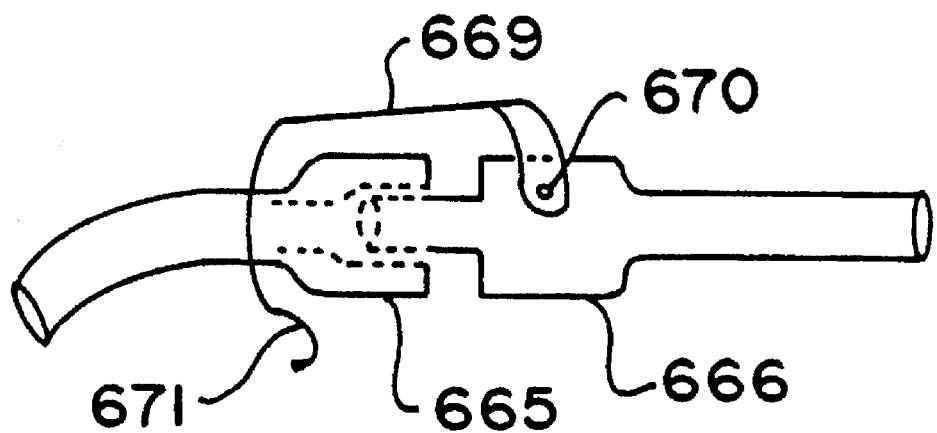
Figure 23A:
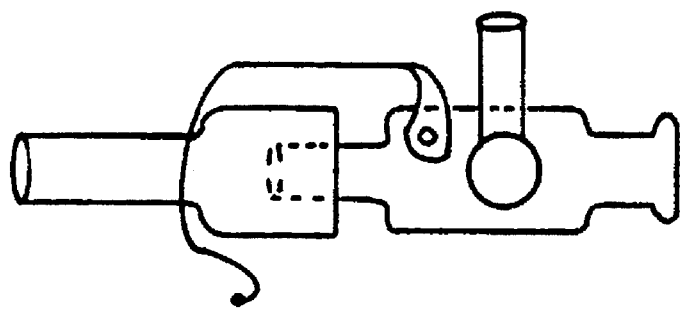

The Groin Model (Please notice FIGS. 21, 22, and 23)

The background: Commonly cardiac catheterization and similar procedures are performed in the groin area. In many of these techniques an artery in the groin and commonly a vein as well are invaded for the insertion of the sheaths and catheters or wires through these vessels. Naturally this perforation leaves an opening in the front or many times in the side wall of the artery or vein that needs to be sealed to avoid bleeding and oozing of the blood. At the present time, this is done by dressing the area with gauze, bandaging and adhesive tapes, and the placement of a sandbag of about ten pounds or so on the area. However, as this inventor has mentioned earlier in his previous applications of D. Device, the above mentioned method is not proper, does not give enough pressure and is not adjustable as well. The pressure can not be measured, controlled, increased, or decreased; the use of adhesives are problematic due to their related skin reactions and pulling the hair at the time of removal. The patient usually suffers because of being confined to the bed without motion for a period of 4–6 hours or so and in some cases even longer. Therefore, the applicant has introduced D. Device: D. Device, D. Device 2, D. Device 3, and D. Device 4. In this application he wishes to make some improvements in those models; he specifies the use of clear (transparent) hard materials to allow the balloon to be pressed against the wound. These means will also use the application of pressure by previously mentioned pre-inflated balloons/bags as well. In these models again the idea of using a wrap or support unit (these may be used interchangeably during this application) is utilized with the difference that the front of this unit will be made from a clear, hard material (could be clear non-stretchable material as well) that will be shaped to match the anatomy of the area or the need. For example, in some models the unit may have a line of depression in the area that will fit the groin line so that at the time of use it will fit the groin line. Also, the unit may have curves to match the curves of the body in the area such as being convex in the lower abdomen and upper thigh area. The edges of the unit may also be bent or curved in order to make a more comfortable unit. It should be said that some or most of these shapes were introduced by the inventor in his previous applications. For example, in the application of D. Device 2, two hard supportive plastic pieces were used in front of the unit. In a modified model of this unit, the unit will be made from two separate hard plastic pieces (or combinations of a soft non-stretchable unit which has an abdominal and upper thigh part that may support a hard, clear piece of plastic in each one of those lower abdomen or upper thigh areas. Each one of these hard, clear pieces may have a curve of its own to match the anatomy of the area which will be used. They may stand next to each other separately in the sides of the groin line or be connected to each other by a different permanent or temporary means such as adhesive tape, hinges, wiring, snaps, Velcro (TM), bands, fabric, thread, or anything similar. This will allow these two pieces to practically or functionally hinge along the connection line. This unit is to support a pressure means or commonly one, two or more units of balloons or fluid-filled bags that are to be pressed to the wound site in the groin or upper thigh area. The balloons which stand under those support units may be connected to each other by a temporary or permanent means. All the balloons or bags and covers and wraps in the groin area will be made clear for better visualization. A third balloon or piece of plastic of any desired shape may be utilized in order to provide more pressure. This may be a wedge shape unit similar to the one shown in D. Device 3 or may have any other desired and functional shape. These parts may also be made completely clear as well for visualization. Importantly, this wedge shaped unit (may be a balloon, sponge, soft, or rigid plastic or their combinations) will be held in place by a wrap or strap that is connected to the sides of the previous unit or the wrap can be separated to go around the body of the patient.

Figure 13A:
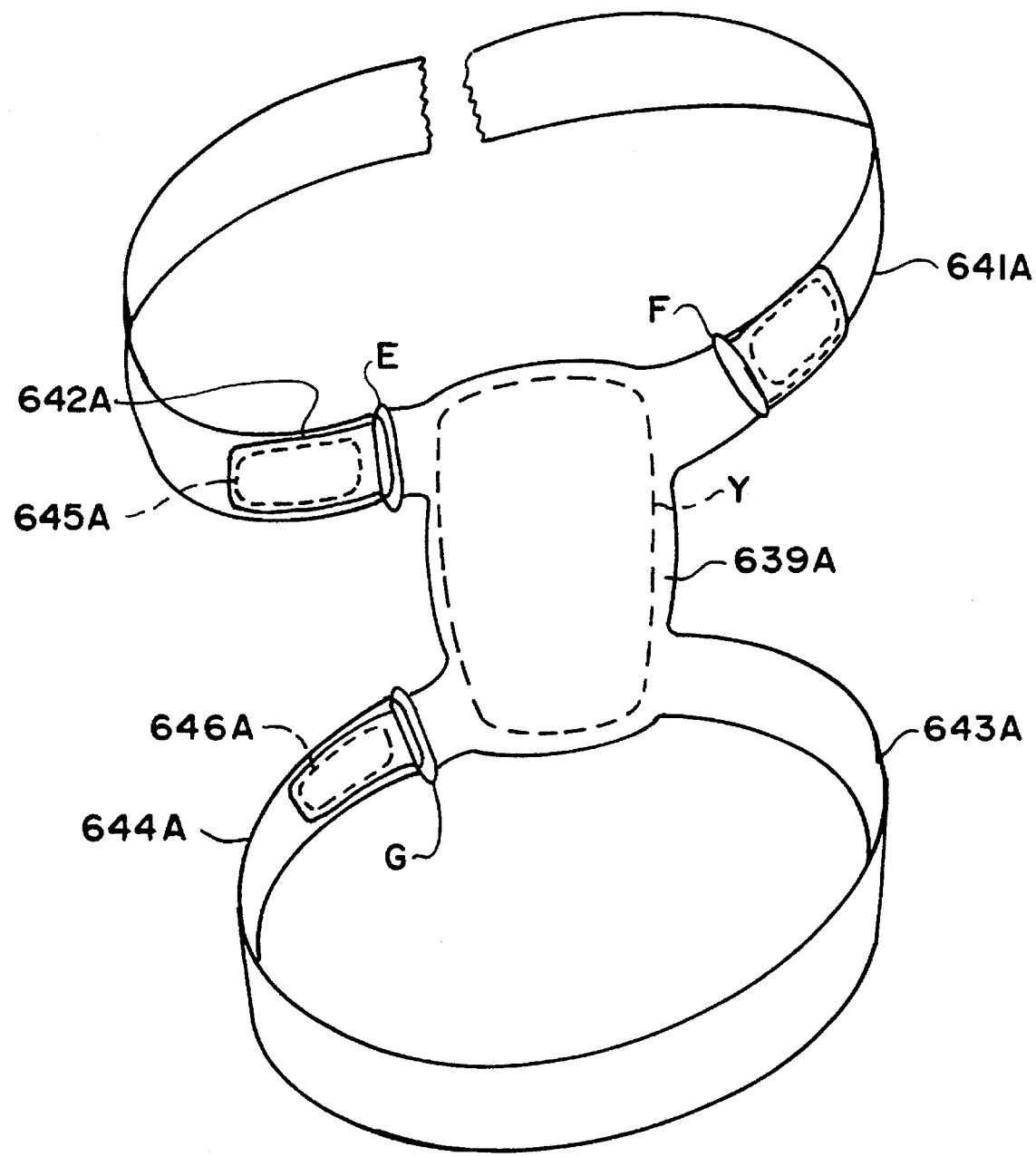
Figure 14:
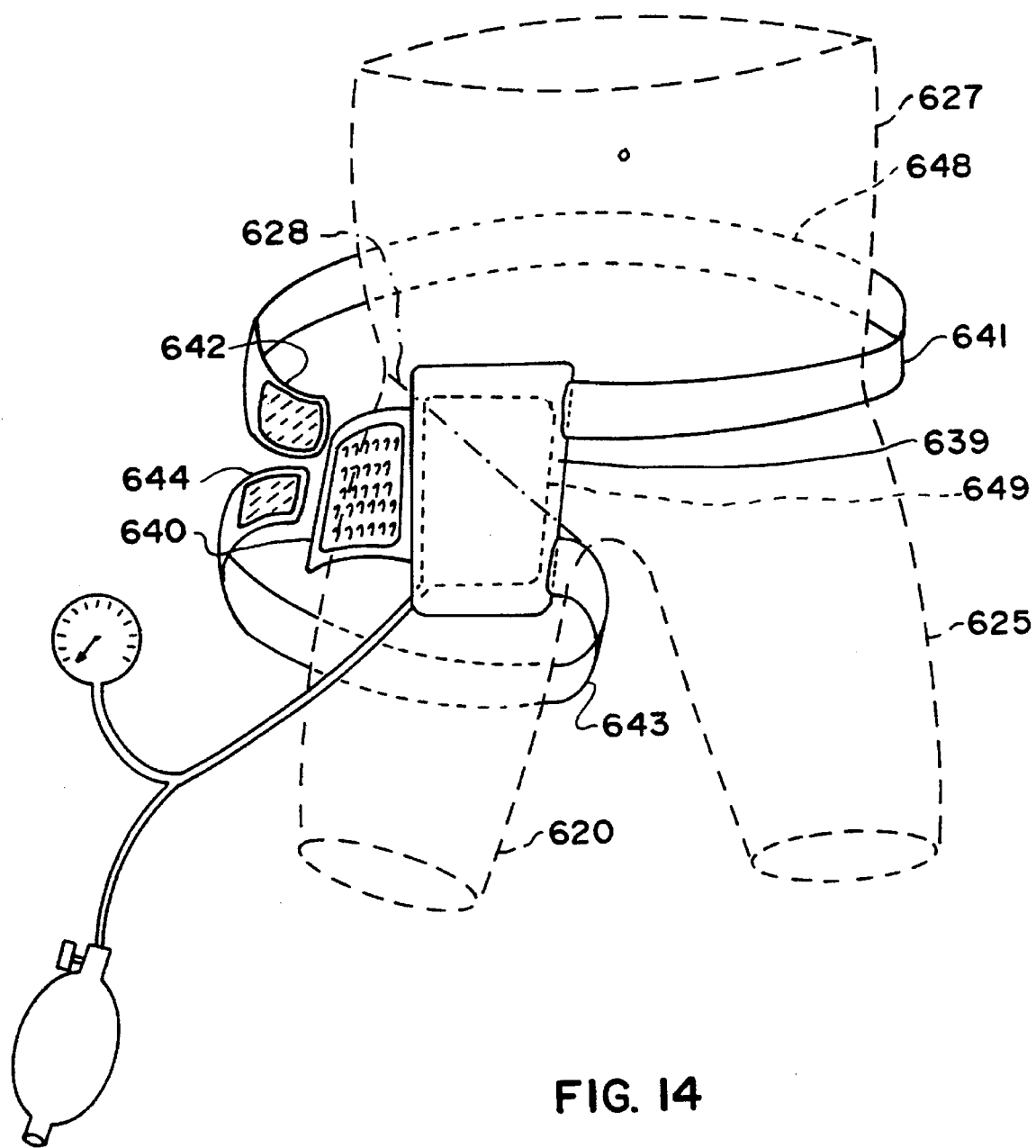
Figure 15:
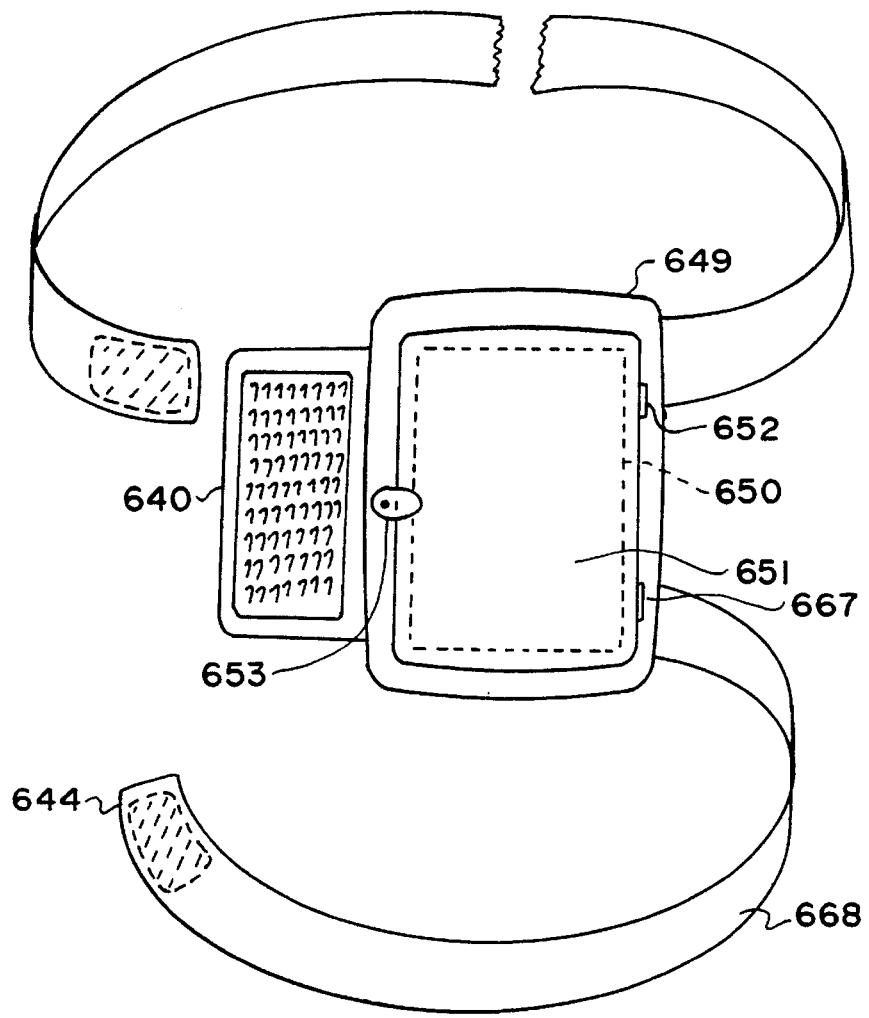
Figure 16:
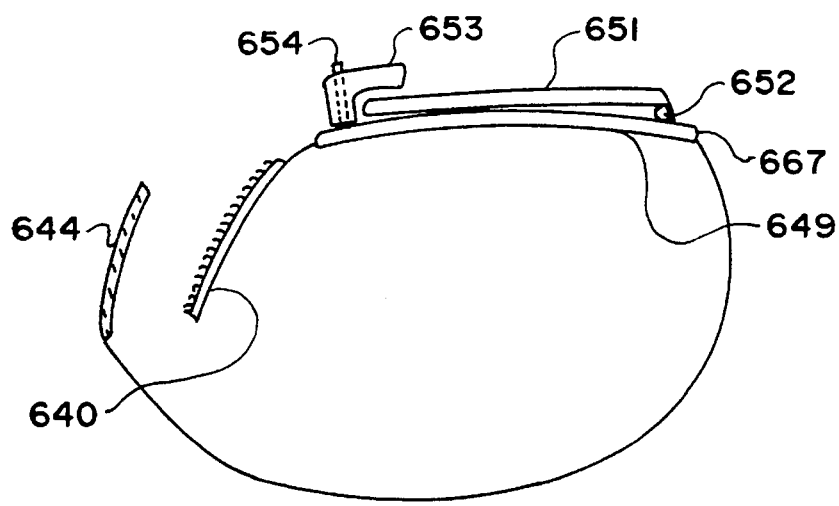

In other models this idea may be achieved by means of using a non-stretchable but pliable support unit, which has a clear front window FIG. 13A no. 639A, stands in front of the groin area, and can be fortified or strengthened by means of a piece of hard, clear plastic or similar material shown in FIG. 13A at Y. This fortification piece or means may be placed to stand under, inside or over this cover. The connection between the hard piece and the wrap may be temporary or permanent. In temporary cases they may be inserted into a pocket or connected by different means such as Velcro (TM), adhesive, snaps, placement under the unit, hinges or any other similar means. Importantly, some polymers may be used that have a high tendency to stick to each other mildly and easily due to a chemical, static, electrical or magnetic attraction, which may be enough in these cases.

Also, a hard, clear, support piece may be used (no 639 FIG. 13) to be the front piece of the support unit. This piece is to be held in place in the upper thigh and lower abdomen area by means of bands, straps or wraps or any similar means and their combinations, FIG. 13 no 641, 643.

Figure 7A:
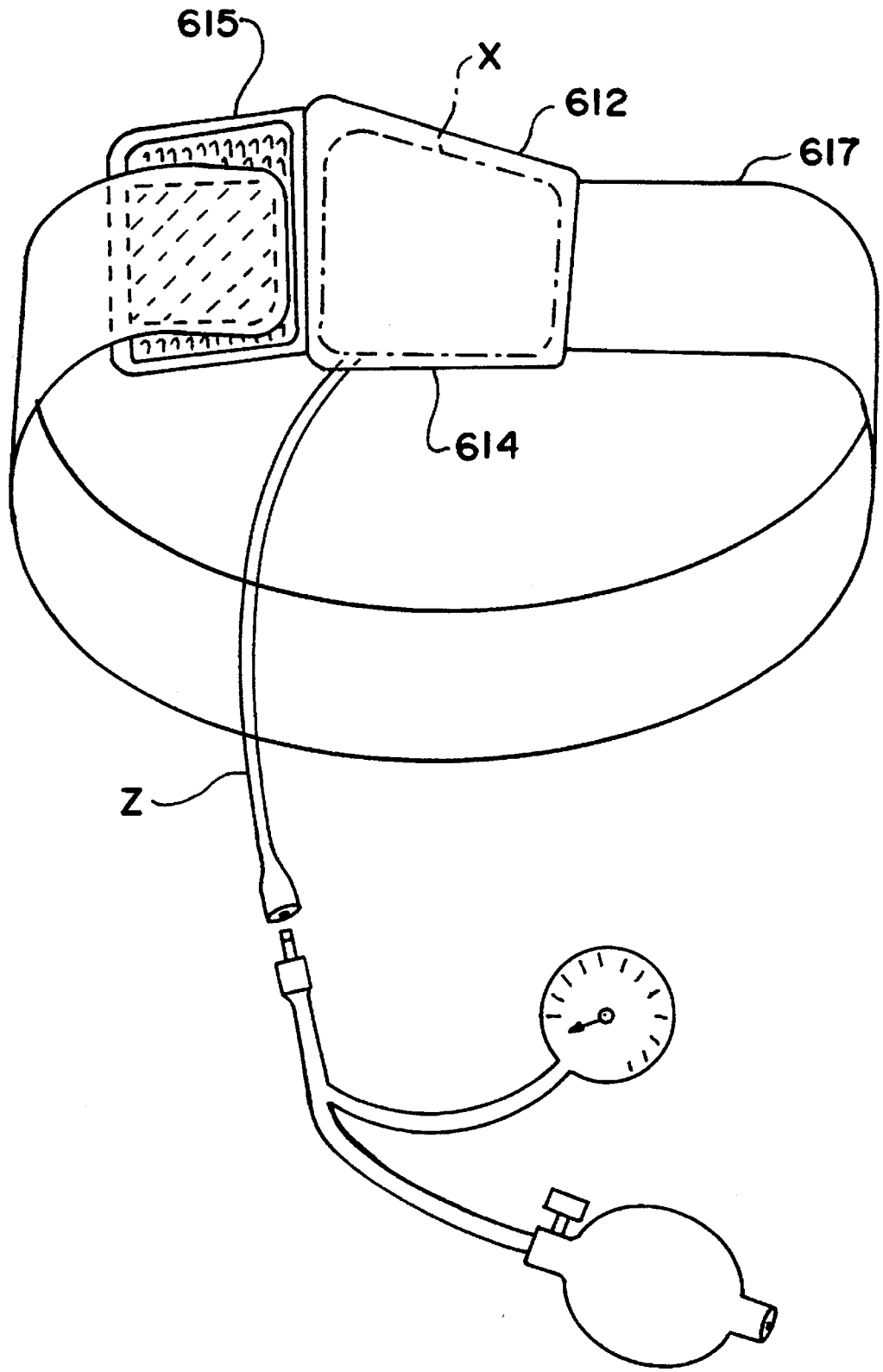

In some models the upper thigh and lower abdominal pieces will be made separately to allow one to be applied in the area earlier than the other one. They may be made to be separate and then to be connected to each other by different means. In the model shown in FIGS. 9, 10, and 11 the upper thigh piece may be placed and applied first on the wound side, then when the patient is more stable the waist=lower abdominal piece (shown in FIGS. 11 & 12 by 633) to be connected to it with ease. This method is introduced since in some cases the insertion of sheaths are done entirely in the upper thigh area and protection of this area will be enough for these particular cases. In some other patients the entrance is much higher and very close to the groin line; thus, protection and pressure of the lower abdomen-upper thigh area in sides of the groin line will be the best approach. Therefore, having different models and alternatives would be the best. The wrap's function in the upper thigh area is essential and vital; it is to support the pressure of the balloon in the wound side. The function of the lower abdominal piece is also very important and additive. Importantly, it would be possible in some cases and models to decrease the size of the abdominal or the waist piece to minimize its size to a band or even to eliminate it. This is so that a strap or wrap of proper size and shape with a clear window or a front piece can be wrapped around the upper thigh area similar to the one shown in FIGS. 7, 8, and 7A. In other words, this unit will be made in the shape of a strap that will be wrapped around the thigh area and be sized properly to have its ends stick to each other securely and to press a hard plate or a pre-charged balloon in the area. This unit will be more useful with a clear window or plate (it can be made from clear soft vinyl as well) in its front to allow the wound site to be seen through the clear window or plate and the balloon. The front piece (the window or the plate) of this unit may be made to have a curve to fit the curve of the area as well. This clear window may be made in the shape of a trapezoid with an oblique side to fit the groin line FIGS. 7 & 8 piece 612. In order to prevent this unit from falling down when the patient stands, the unit may have a soft non-stretchable piece connected to its upper border to be held in place by a strap going around the waist line FIG. 9 no 623. The end pieces of these straps or wraps will be stuck or fastened to each other by the following means and methods:

a. Adhesives may be utilized to stick one end/ends of this unit to another.

b. Use of Velcro (TM) patches or loops and hooks for this purpose to allow easy connections of the ends.

c. Use of different methods of fastening such as a belt system and appropriate buckles, snaps, or any other similar means.

d. The use of adhesives tapes that will go over the ends which are brought to each other.

e. Many forms of reversible connections may be used in this regard to allow the ends of the straps or wraps to be held together easily and reversibly.

The whole strap or wrap may also be made from a clear material such as latex, vinyl, a polymer or any other clear synthetic material. This unit may be made to have a soft lining as well. They will be shaped properly to fit the area. Importantly, combinations of materials may be used as mentioned earlier.

The connection of the balloons and the wraps can be either permanent or reversible, and the following means may be used:

1. Use of Adhesives
 2. Velcro (TM) patches
 3. Snaps
 4. Similar other means so that the balloon/balloons can be separated and stuck again.

5. Use of chemical, static attraction, or magnetic power.

The balloon may be part of the construction of the wall of the wraps, or stuck to the inner wall of the wrap to be ready for use. The temporarily connected techniques will allow different size and shape balloons to be utilized with a given wrap in order to match the individual need of a particular patient.

The nature of the wraps may vary and the following alternatives are possible:

I. The wraps may be elastic when the need for pressure is not high. This will be made for the upper thigh area; elastic materials may also be used in construction of the shorts.

II. The models are to be non-stretchable. These are mostly when a higher degree of pressure is needed. These wraps are to be strong in the front (either by their own strong materials or by adding a hard clear plate so that the combination will be strong and proper enough) to support a pressurized balloon, fluid filled bag or any other means for pression the wound area such as a screw/lever-plate system, hydraulic system, a piston system or any other similar methods and means that will allow pressure on the wound site.

III. This support system may have a piece of clear, hard plate in the front held by straps connected to its sides or corners of this hard piece to support a pressurized balloon, fluid-filled bags or any other means for pressing the wound area such as a screw/lever-plate system, hydraulic system, a piston system, or any other similar methods and means that will allow pressure on the wound site.

IV. In some cases combinations of the elastic or stretchable and non-stretchable materials may be used. Previously, the inventor has introduced a special type of this combination in D. Device 3. In that case the main unit is made from elastic materials; however, combinations of non-stretchable materials will be used as well, allowing the creation of different units.

Importantly, "tabs" will also be used and placed on the outside surface of the wraps to allow the wraps to be pulled and positioned as required (FIG. 40). In such cases the outside surface of these wraps in certain places or throughout may have tabs of elastic or fabric. These may be made of the same material as the wrap or it may be of a different nature in order to allow these tabs to be held to pull the underlying wall easily from the skin in order to adjust the wrap's position with ease. Furthermore, these tabs may also be made to be pulled and connected to each other or to be taped to each other or the outer surface of the wrap itself in order to adjust the length of the wraps. Importantly, the use of such tabs for holding is so beneficial that even the non-stretchable wraps may be made to have such tabs on their surfaces in needed areas to help handling and positioning them.

An overview of the wraps was previously mentioned and the general idea will also apply here in this unit as well.

This wrap=support unit will be strong and supportive to tolerate the pressure generated in the area by a balloon or different means. An inflatable or a pre-charged balloon/bag may be used and the balloon/bag may be filled with air, fluid, or gels. The pressure in the wound area may be generated by pulling the non-stretchable support to press the balloon/bag on the wound site. The end of the strap or wrap may be connected to the end of the other side by different means of it can through a strong and sturdy band or bridge to make a U-turn and come and be stuck to its rear side and fastened there securely by various methods. This technique will be strong enough in certain cases such as stable patients after catheterization or cases that are stable to be discharged from the laboratory or the unit. When using this method the amount of pressure on the wound area may be altered based on tension applied to the wall of the wrap and how much it is pulled. However, in other cases more pressure or alterations of the pressure may be needed which can be applied by utilizing the following means:

a. By pulling the sides of the band, strap or wrap that covers and supports the area or the pre-charged balloon.

b. By making the bands, strap or the wrap from elastic materials strong enough to pull the balloon or the bag against the wound to keep it tightly in place.

c. By use of an inflatable balloon "A" to be placed between the non-stretchable band, strap or wrap and the balloon/bag "B" that can be separated by a hard plate. This is so that the inflation of the balloon A will press the balloon/bag toward the wound site.

d. By incorporating a piece of spring between the non-stretchable band, strap or wrap so that the base of the balloon/bag will press against the balloon/bag when it is held tightly by the non-stretchable wrap.

e. By screwing a large and specifically constructed screw means or system to push a hard plate against the balloon and to hold and press the balloon on the wound site. In some cases this flat clear piece may be directly pressed on the wound area so that it will prevent bleeding.

f. By pressing a hard plate toward the balloon by lever means or system so that it will press the balloon to the wound site.

g. By use of an air-filled balloon which is pre-charged and will be placed and used over the wound area to act as a buffer or to keep the pressure by having its inner air being squeezed by the pressure of the pulled non-stretchable wrap.

h. By use of a unit from a fluid or gel-filled bag that has a series of small air-filled bubbles inside it so that they act as a buffer and to keep the pressure by having its inner air being squeezed by the pressure of the pulled non-stretchable wrap or even an elastic wrap.

I. Any other methods or possible means may also be utilized in this area to serve this purpose as well.

These methods will allow pressing the balloon or a fluid filled balloon/bag on the wound site.

Importantly, the use of pieces of plastic, especially transparent plastics, is of interest to provide vision. These pieces may be hard and with the shape or curves to match the shape of the area. The use of a small flat piece of clear plastic in the area under the balloons is of great importance in order to provide what the inventor indicates as providing a rather solid pressure to the area; this is to prevent focal or localized pressure to one spot that can be damaging to the vessel or the area. A focal pressure can stop circulation of the blood and also may cause phlebitis.

Other models of pressure producing systems such as the screw/lever plate system may be used as well. Importantly, the system of pressing by screw/lever plate may also be used with smaller wraps to protect the wound site at the time of ambulation or discharge. This system may be mounted on the wall of a short, shaped support unit as well as be used at the time of discharge of the patient from hospital to provide the needed physical and psychological support.

When considering the use of using a screw/lever-plate system it should be noted that in such cases in order to have the wound site visualized well the screw may be made to press the base of a frame with four feet, each standing in one corner of the lower plate so that the center of the unit is left clear.

The Balloons And Their Particular Shape For This Area

The balloons for the groin area will primarily have the same characteristics mentioned above in this application with some modifications to fit the area and the purpose.

It is to be said that the function of these balloons is extremely critical for this unit and it is important to notice that all types of shapes, makings and constructions of the balloons mentioned earlier in previous applications of this applicant will also be utilized here. Special reference is made to the shape of the balloons in D. Device (FIGS. 3, 5, 8) and D. Device 2 with particular interest in FIGS. 1, 2, 3, 5, 6, 7, 8, 9, 10, 11, 14, 16, 18, 19 and 20. Also, figures from D. Device 3 with particular interest in FIGS. 1, 2,3,4,5,6, 7, 14, 15 and 17 and in Device 4: FIGS. 4, 5, 6, 7, 8, 9, 12, 13, 14, 15, 20, 22 and 23 regarding the balloons. A copy is included for reference.

The general specifications of the balloons mentioned here in text will be followed for making special balloons for the groin. Basically, these balloons will be made from a clear, soft polymer to allow the best vision of the wound site. These balloons may have a round, oval, triangular, rectangular, rhomboid, half moon or any other possible and needed shape. These units may be made to be flat or their thickness (the size of the balloon from the front to the rear) may vary from a narrow size to a thick unit during the width of this unit and also during the course of the balloon as well. The thickness as well as the softness of the wall of the balloons may vary; it may also vary from one wall to another or one particular part of a wall to another to allow different extensibility. The balloons may have one or two inflation tubes with an end similar to the male or female ends of an intravenous tubing so that universal connectors may be attached. It may also be connected to a three-way stopcock or other kinds of valves. This valve may be chosen to be a one-way valve. The one-way valve may be chosen to be next to a three-way stopcock in order to allow inflation to occur by an inflator and then deflation to be done by the three-way stopcock. An alarm unit or alarm system may be used; this alarm may be of any kind. The alarm model mentioned in D. Device may also be used. A gauge may be utilized for measuring the inside pressure of the balloon.

The alarm system may be chosen with different interests and programs. Importantly, advanced electronics and micro chips technologies may be utilized to allow multiple control, programming, and alarming systems to be made. These will allow information to be given or alarms to sound if there is an unwanted change of pressure inside the balloon or any other unwanted changes. The pressure gauge and alarm system may be separate or combined. The pressure inside the balloon may be programmed to be dependent on the pressure of the patient. It may also be programmed to slowly decrease the pressure inside the balloons based on the program. These will all allow making a sophisticated unit to serve the need best.

The rear surface of this balloon may be chosen to be flat or curved, with a variable thickness and consistency. It may have a hard rear surface in order to prevent bulging outward, which can be used with a soft non-stretchable support unit. The alternative will be using a wrap or support unit with a hard support in front to support a soft balloon.

The front surface of this balloon will face the wound area. Importantly, this surface will be made to be soft to expand and in some cases to assume the shape of the area, or to fill the creases and spaces between the tubes, sheaths, or certain tissues, etc. Importantly, in some cases the front surface of this balloon may be covered by a hard or semi-hard clear plate in order to provide a flat pressurized area to the surface of the wound. Alternatively, this flat plate may be stuck or glued on to the surface of the balloon or even placed on the skin over the wound area to function as planned. In some cases a piece of gauze pad may be stuck on the front surface of this balloon. This gauze pad may have a plastic base to prevent wet and contaminated materials and secretions from going through it. This gauze pad may have a film of adhesive on its rear surface to allow it to be stuck on the surface of the balloon. Thus, importantly, this balloon will be made in different sizes and shapes such as triangular, rectangular, rhomboid, oval, circular, half moon, half oval, ring shaped, ring shaped with one side open. Combinations of these or any other shapes, thicknesses, and sizes that will perform well for this area and the purpose will be used. Any other possible desirable and useful shapes for this purpose may also be used to provide the freedom of using it in different people with different body sizes as well as different shapes in the site of use. Of special interest is using combinations of balloons in the groin area so that each will do a particular function. For example, one balloon may be placed on the upper thigh area; another can be placed in the lower abdomen area. Each will be on one side of the groin line so that after inflation they will allow the hip joint to bend in the area without compromising much of the pressure. This technique is also mentioned in D. Device 2. The time of discharge is now of great importance since with some mild modification they can also be used effectively in the acute phase as well. Such units will allow the patient to sit more comfortably without losing support. These models will also allow each one of the lower abdomen and upper groin area balloons to be used alone independently. Pieces of hard, clear plastics of different shapes and sizes may be utilized and placed on the rear side of the balloons to provide more support and shape in these cases. Such hard plastics may be placed on the rear surface of the balloons over, under, or inside the front wall of the wraps, to be either temporarily or permanently connected to it, or to be part of the rear wall of the balloons or an actual part of the rear wall of the balloon itself.

A particular model of this unit will be made with a hard piece in front made from clear plastic in the front which may be mostly in the shape of a trapezoid as shown in FIG. 11. The oblique side of this piece 613 is to fit the groin, about the groin line 628, and to have an upper part 623 that will be non-stretchable but soft to stand in the lower abdomen area as shown in FIG. 11 as well. Then the sides of this hard piece will be connected to a strap Y (the groin strap) shown at 617 from one side and to a flat surface Z shown by 615 made from soft or semi-hard, non-stretchable material from the other side. The strap 617 is to wrap around the upper thigh area, come around, and its ends will be connected to the piece 615 by a means of fastening (here Velcro (TM) patches are used). The oblique side of this unit no. 613, FIG. 11 will be connected to a soft, semi-hard or at times hard piece in a shape shown at 623. This will have patches of Velcro (TM) on it. This piece will accept the Velcro (TM)-patch-covered inner surface of the strap 633–635 shown in FIG. 12 (this may be made from a loop part of Velcro (TM) as well) in which its sides are to wrap around the lower abdomen or the waist area and to come and be connected to its own end to make a circle. The strap 633–635 (the abdominal strap) is to function to participate in securing the unit in place by:

1. Preventing the unit from falling downward if the person stands up.

2. To support piece 623, which may have a piece of hard plastic or a piece of hard plastic placed under it to create pressure by an inflatable balloon. This balloon is to press the area in the lower abdomen close to the groin line.

Figure 17:
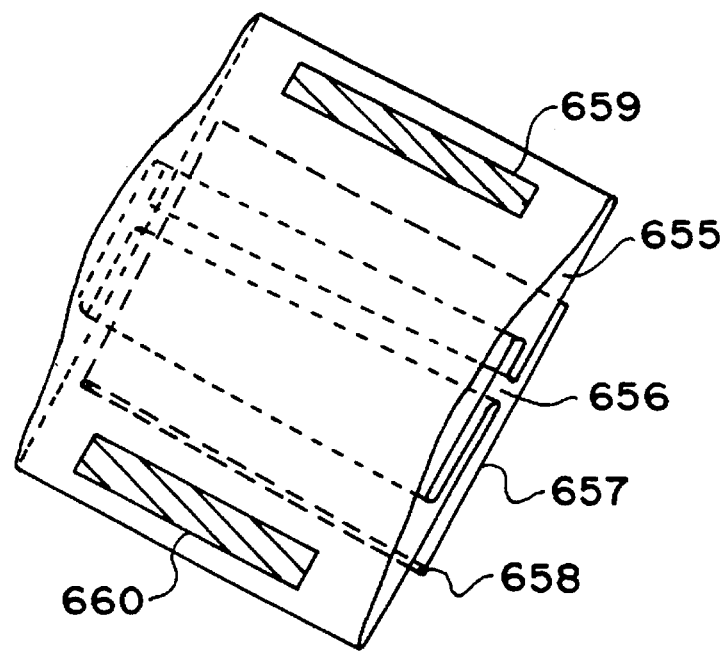
Figure 17A:
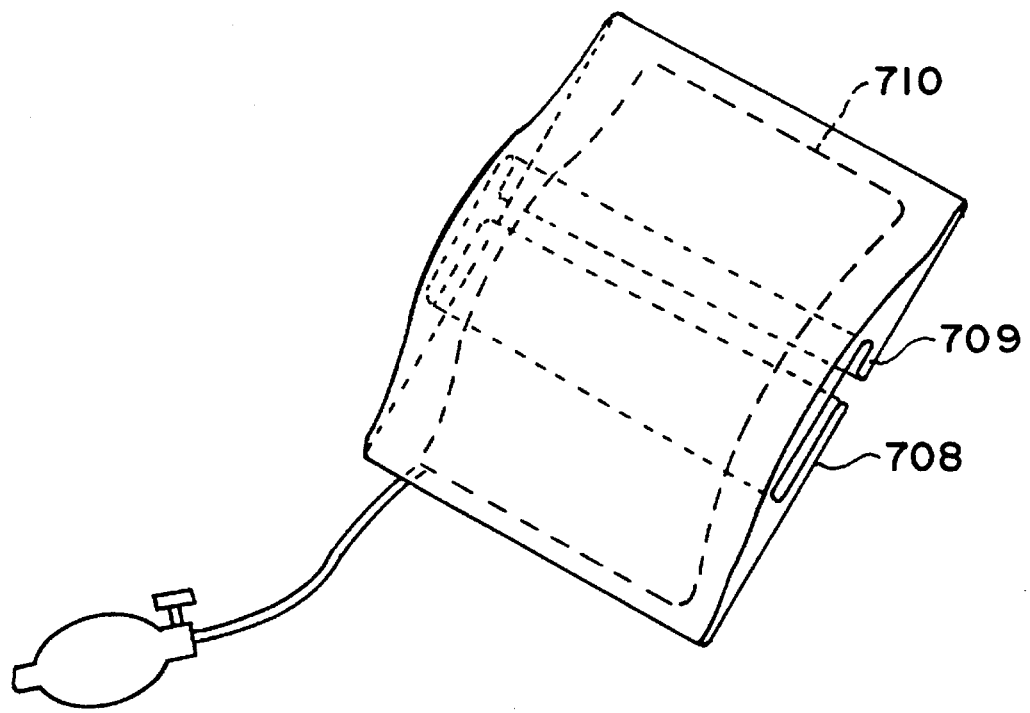
Figure 18:
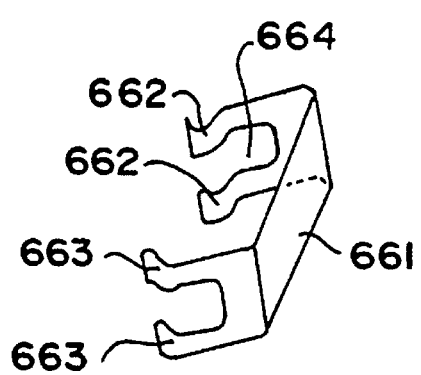
Figure 19:
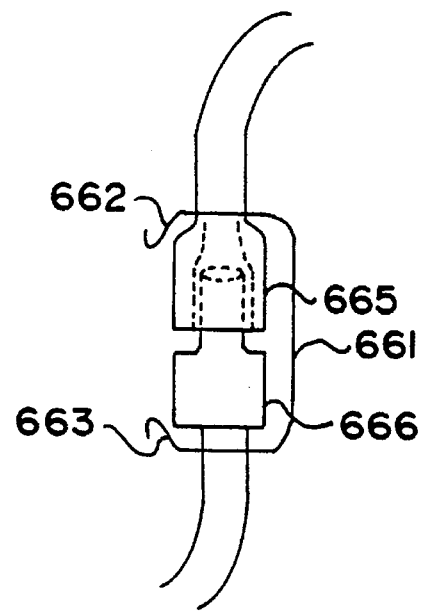
Figure 20:
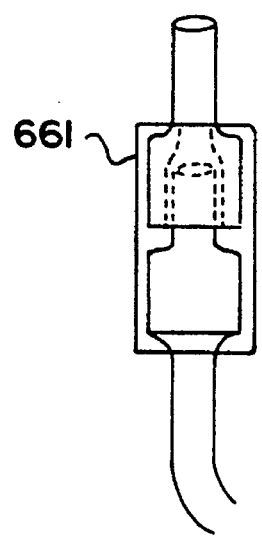

This model which is a separable upper thigh and lower abdomen unit as shown in FIG. 11 is clinically very important since it will allow the thigh unit to be placed first and the balloon to be inflated. Then, when the patient is more secure the lower abdominal strap can be connected. Importantly, this unit may even be fortified with the use of a back support (FIGS. 17 & 17A). This back support will be made from an inflatable balloon which has a flat, hard rectangular or similar shape in the back and is designed to bulge toward the front. The rear part of this back support will have a tunnel or similar means to allow a wrap or strap to go inside it and be pulled easily without friction. Importantly, since this may be placed on the X-ray table this will be made transparent for the X-ray. It will also not have particles that disperse the X-ray in different directions. This unit may also be made to allow water or fluids of a different temperature to be filled or circulated inside it—mostly warm water to allow the patient's back to rest and to relax and be comfortable. Importantly, a piece of hard plastic plate of any shape, thickness or consistency on the front or alternatively to have a similar piece stuck or attached to its front to allow the shape of the front wall to be modified in any desired way. This is important since this will take effect in the area of the wound in which the pressure is being applied. For example, one part of this area may be chosen to be protected, shielded or commonly and as mentioned earlier to avoid pressure to a relatively small area. Importantly, the applicant is specifically avoiding giving a very specific number in the size of these pieces, and wishes to give his opinion: In general, the applicant's reason for such action is not that he wants to give an ambiguous statement, but the fact is that the sizes are relative. In the case of a new born being catheterized; an area of half inch diameter in his/her groin is a large area compared to the size of the body while for a large 290 pound 6 feet and 1 inches tall person is very small. That is why a given size for such units does not seem to be scientifically correct for the applicant and thus only the whole idea is introduced here.

The separable upper thigh and lower abdomen unit is a very important and convenient technique since it will allow the thigh unit to be placed first, the balloon to be inflated, and then when the patient is more secure to have the lower abdomen strap connected. Importantly, other precautions are advised in some cases for prevention of blood clot formation in the legs. For example, with this unit the patient will first be advised to raise his/her leg, do some leg exercises and to keep it raised for some period. Secondly, in some cases even an external compression device will be used to diminish the chance of blood clot formation in the legs.

Also, importantly, in some models the front wall of the unit may have a special opening in the wrap as well as the balloon to allow use of a Doppler probe to evaluate the circulation in the groin area.

Importantly, the function of fastening the ends of this unit may be done by a special means of using small bubbles, tubes, or small units of plastic that will hold enough amounts of adhesive inside and will allow it to be dispersed under pressure. In this case the squeezing of the two pieces that are to be stuck to each other will be enough to create the release of glue or adhesive material into the space between these two layers and to attach. The degree of the stickiness would depend on the amount and strength of the adhesive which is used. It may be chosen to be weak and reversible or it may be chosen to be strong and lasting. This will be of unique value in these units in allowing the ends to be placed in any spots that are feasible since, importantly, it is not possible in a given patient to know where the end of the strap is going to end to have the fastening material be placed on that spot. Also, using long Velcro (TM) patches may not be economical. These units of adhesives may be placed in lines or series so that a reasonable area will be covered to produce enough strength. The shape and size of these pieces can be different. These can also be placed on the back of Velcro (TM) pieces so that the combination will allow a very easy placement of Velcro (TM) patches on a needed area. The inventor believes the suggested technique will be very helpful in many medical or other uses in connecting the pieces to each other without the need to peel another layer. [This can be extended by making other means of attaching the pieces of material to each other. One simple way would be using a special series of spikes that will easily go through a fabric but would not come out due to its special one-way arrow head shape.

These units will be of great value in the prevention of bleeding in the intervention sites and of help in such patients. Some of these benefits were explained above and may be mentioned briefly as follows:

1. The pressure of this unit is easily adjustable, is not gravity dependent, and would not limit the patient to one position.

2. This unit will practically eliminate the heavy use of adhesive tapes and adhesive chemicals and will reduce the patient's pain, untoward reactions, and cost as well.

3. When used for the groin after cardiac catheterization, this system will allow patients to sit, stand up and move sooner. Patients will suffer less and be discharged earlier.

4. The temperature of the balloon/bag of the unit can be chosen to be cold or hot for a cold or warm compress in the area.

5. This unit due to its inherent protection and safety will allow the patient to be discharged home earlier so that he/she can avoid bad driving (especially in the winter) and to return to his/her job sooner. It would also cut the need for medical supervision to diminish the cost of hospitalization.

6. This unit will prevent the patient's anxiety and fear from possible bleeding and wound area damage as well.

A Unit For Being Used Prior To Ambulation And Discharging The Patient Home

These are special units designed to be used before ambulation and/or discharging the patient home. In general, there is a concern about the safety of such a patient during this period since many factors such as the use of anticoagulants, increase in blood pressure, increase in intra-abdominal pressure due to cough, vomiting, straining, etc, may cause bleeding after the initial period of stabilization is over. Also, there is the fear of patients and medical staff that bleeding may occur later after discharge; naturally it would be best to prevent bleeding. Another motive for this inventor for introducing this unit has been the potential benefit which a continuous pressure may provide for prevention of long term complications in the site of interventions. He believes that if bleeding is prevented, hematoma, tissue damage, and other major problems such as pain, discoloration, discomfort, inflammation and even A– V fistulas may be prevented as well. For this reason he believes it is wise to prevent potential bleeding which may occur during the period of ambulation or transferring from the clinic. To satisfy such concerns and problems the following units were introduced earlier by this inventor in D. Device 2 and D. Device 4. These units are to support an inflatable or precharged balloon or a special shaped piece of hard, clear, flat plastic in which this plastic piece may be attached temporarily or permanently to the front of the support unit. In simplest form this support unit may be made from a strap or a wrap to wrap around the site of the wound in any place, such as the antecubital, groin, or any other similar places, in order to support and press the wound site and prevent bleeding. In this simple model, a properly shaped strap which has a clear front wall may be utilized for this purpose. (A model of this unit for the upper thigh in FIG. 7). The ends of this strap will be brought together and be held securely by means of proper fastening such as adhesives, snaps, Velcro (TM) patches or similar methods as mentioned. In some models in order to prevent the unit from falling, the surface of the strap or wrap may have bands of adhesives covered by a protective layer to be peeled off before use. However, mostly this goal will be achieved by having an abdominal or waist piece to make the unit more stable or even a strap to go around the neck or shoulder area like a suspender. These pieces will keep the unit in place securely and prevent it from falling when the patient stands up. The clear window in front of this unit may be made from an open window, a soft or hard plastic.

Here to specify more about these models for ambulatory use the units that can be used in the groin is specified, although the same basic ideas may be used for making units for the other places as well. Such units are as follows:

a. A strap or a series of straps will be made to go around the wound site on the upper thigh singularly or in combination with a waist= lower abdominal piece, so that by being wrapped in the upper thigh area this unit can create, maintain and support pressure or units such as gauze, pressurized balloons, bags, or things of that nature in the wound site. This unit will preferably have a clear window in its front to allow visualization of the underlying area. It may also have a hard, plastic part for further support in the wound area. The ends of these units can be fastened by Velcro (TM) patches, snaps or other means of fastening mentioned above. This unit may also have a door that can be opened to provide direct access to the wound. These straps may be made from non-stretchable, elastic materials or their combinations.

b. A wrap will be made to go around the thigh singularly or in combination with the waist (lower abdomen piece) piece to create, maintain and support pressure, as well as supporting units such as: gauze, pressurized balloons, bags, or things of that nature. This unit will preferably have a clear window in its front to allow visualization. It may also have a hard plastic in front to provide more support in the area. The ends of these units can be fastened by the means of snaps, adhesives, Velcro (TM) patches, buckles or similar means. Some models of this unit may also have a door that can be opened to provide direct access to the wound.

c. By use of a pair of tight, elastic shorts that can be worn so that its elasticity will hold the needed materials for preventing bleeding such as pieces of gauze, balloons, bags, etc, in place. This unit may also be made to have a clear window in its front to allow visualization of the wound site. It may also have a door that can be opened to provide direct access to the wound as well as a piece of hard plastic for supporting the balloon and bags. This hard plastic may be connected to the shorts' wall by a temporary or a permanent means. In temporary cases the hard plastic may be connected to the shorts by means of snaps, adhesives, Velcro (TM) patches, buckles or similar means. The wall of these shorts may be further strengthened by the use of one or more straps going around the shorts in the upper thigh and lower abdomen area. These straps may be separate and independent from each other. For example, one strap is for the lower abdomen and one for the upper thigh area. Their sizes and shapes may vary as well. Importantly, these straps may also have a piece of clear material or can be made from a clear material such as vinyl or plastic to allow visability of the wound.

These shorts may have openings on the front and back to allow for physiological needs such as passing urine bowel movement. A proper flap or cover may be used to cover these openings.

D. By making special shorts which are large and comfortable, with a front part that is clear as well as acting as a support for balloons or bags of proper size in their walls which will be placed on front of the wound area, and will be further supported by a non-stretchable straps or wraps, so that the needed pressure in the area can be maintained. The connection of these bands, straps and wraps to the wall of the shorts may be accomplished by different temporary or permanent means such as sewing, adhesives, sticking, using velcro patches, snapping, hooking, stapling, or similar means. These straps/wraps are to be clear or can have a clear front part to allow observation of the wound. There will be a strap/wrap to go around the upper thigh and another one to go around the lower abdomen area. However, in some cases the lower abdominal piece may be replaced by the belt and support system of the shorts itself. A further band/strap may be used to go around the neck or shoulders for further support. A suspender system may be used for a further means of holding the shorts in the proper place and preventing it from falling or being uncomfortable. The ends of these wraps may be connected by the fastening means mentioned above. Also, in order to fasten these wraps securely, the ends of the straps/wraps may go through a hook or a bridge on the surface to make a U-shape turn and then to come and stick to its own side.

Importantly, in some models the wrap or support unit may also have a part, segment or bands of elasticity in its construction to provide a pulling effect in the wrap for this use (this model will be used mostly with the pre-charged balloons).

A hard, clear plastic piece may also be placed on front of shorts either temporarily or permanently to provide more support to the area. This piece may be placed inside a pocket on the front wall of the shorts as well.

These shorts will hold one or more inflatable balloons in place. These balloons may be precharged with air or fluids, but importantly it will have the construction and capacity of being inflated later to provide pressure to the wound site if it is deemed necessary.

Importantly, a screw/lever-plate system similar to the one mentioned in previous application of D. Device 4 may also be utilized for pressing the wound site. This will be utilized with the wraps, and shorts as well. This will provide the needed pressure in the wound area for prevention of bleeding. In some of such models when only the pre-charged balloon/bag is used, a piece of spring may also be sandwiched between the base of the balloon/bag and the inner wall of the shorts or the straps/wraps as well to help in building and maintaining pressure in these areas.

The shape of the balloons may vary, especially flat, clear balloons of any shape may be used. The shape of the balloons may be flat with a rectangular, half moon, or any other particular shape that will be needed. These balloons may be chosen to have an outer surface that is hard, strong, and supportive and an inner surface that is soft and expandable. They may also be made from a soft balloon that will be caged inside a specially constructed and needed cover. The front of these balloons may be made to have a piece of hard plastic plate of any shape, thickness or consistency in its front or alternatively to have a similar piece stuck or attached to the front to allow the shape of the front wall to be modified in any desired and useful means.

Units For The Subclavian Area

Such a unit was previously mentioned in D. Device 4 and is primarily designed to be used after conditions such the removal of the Swan Ganz catheter or pacemaker wires in the subclavian areas to prevent bleeding. These units are to save time, be more effective and to diminish or eliminate the use of adhesives. For this reason previously in his application for Pressure bandages and dressings, and D. Device 4 units were introduced to be used. The inventor is referring to these materials, particularly materials related to pictures 5, 6, 7, 8, 9, 10 and 11 from the application of pressure bandages and dressing. However, in this application the applicant wishes to stress a few important points such as the following:

1. The unit or at least the part which stands in front of the wound site will be made to be clear to allow direct visualization of the wound area.

2. The unit may have a piece of hard support in its front surface or the rear wall of the balloon.

3. The supportive wrap or strap may be made from separate pieces that can be connected to each other.

4. The unit may be made to be elastic or from non-stretchable material.

5. The unit may use a precharged or inflatable balloon or combinations of the balloons.

6. The unit may use a fluid-filled bag instead of a balloon.

After this introduction it is to be mentioned that many models of such units for subclavian areas may be made. These units will have a wrap (FIGS. 13 & 16 of D. Device 4) that fits the shape of the area (namely subclavian area) going around the armpit of the other side to the shoulder area to make a sturdy, comfortable, effective support unit and allow pressure to be built. The wrap may be made from a non-stretchable material (especially clear vinyl) as well as elastic materials (especially from latex) which assumes the shape and anatomy of the area easily. A soft layer of cotton or a soft fabric may be used as a liner to provide more comfort. This wrap will be shaped to be secure in the area and to support an air-filled or fluid, liquid or gel-filled balloon/bags to be held tightly in the wound site for pressure application. These balloons or bags will also be properly shaped to match the surface of the wrap. Importantly, the rear surface of this balloon may be made to be hard and supportive but the front surface will be made to be soft to assume the shape of the area (the degree of this hardness may differ in each case and has to be chosen). In some cases or models this balloon/bag may also be made to have/or to use a piece of spring (which may be made to be flat like a cake of spring) in its rear wall to provided the needed pressure. It is also possible to make a spring, a balloon or a bag to be pushed by a screw/lever system as mentioned, so that the unit will provide a nice and comfortable means of pressure application and prevent bleeding and its related problems in this area. This unit may also be used in other chest wall lesions as well when it can be properly utilized.

The units for the wrist area. Such units are to be utilized after removal of the arterial line from the wrist or after certain surgeries and conditions in this area in which the use of this unit will be beneficial. This unit will save the medical staff's time and will be quite effective as well. Such a unit was introduced by this inventor in his previous application of D. Device 4. Basically, these units will be made from a special wrap such as the one shown in FIG. 20 of the application of D. Device 4 that will fit and match the shape and anatomy of the area. This wrap will wrap around the wrist and base of the hand as well and will have a piece to come through the space between the thumb and the second finger and then to connect to the other pieces of this wrap or support system in the rear surface of the hand and wrist by adhesives, Velcro (TM) patches, or similar fastening means. This wrap will be made from a non-stretchable material or an elastic material such as latex or their combinations. This whole wrap or at least its front part will be made clear to stand in front of the wound area and allow observation to occur. This wrap will be shaped to be secure in the area and to support an air-filled, fluid or gel-filled balloon/bag (FIG. 20 no 99 for D. Device 4) that will be properly shaped to fit this area and fill it. This wrap may also have a piece of hard, clear plastic to attach to it temporarily or permanently and to provide more support to the balloon. Alternatively, the rear surface of this balloon may be made to be hard with a shape or curve to match the anatomy of the area, but the front surface will be soft enough to assume the shape of the area. The balloon may be stuck to the wrap temporarily or permanently or it may be incorporated in its wall to be ready for use.

The balloon or fluid-filled bags will also be made to be transparent. These units may be made basically from softer plastics with/without a soft comfortable inner lining to prevent skin discomfort.

Importantly, a modified version of this unit may be made to hold and support an arterial line in the wrist area. In this case the unit will use a rigid piece or cradle in its front that will allow and accept the base and the tubing of the arterial line to be placed inside it safely and also will have a rigid construction to prevent the wrist joint from motion. This unit may have a small properly shaped precharged or inflatable balloon placed under it and over the skin of the wrist over the artery to prevent oozing blood as well.

Use of this unit in other areas. The units mentioned above may be altered and modified to be used in many different areas of the body in different conditions such as after surgeries or wounds when its function could be beneficial. This unit may be used to prevent bleeding in areas such as limbs, body sides and even the scalp, etc, because of its effectiveness and versatility. The support can be made from any shape to hold a pressurized balloon in place. The fact that an elastic support can be used is of important advantage since it will fit the anatomy of the area best to hold a proper balloon or bag in place. The fact that such a support may have tabs of different shapes, sizes, and natures in their outer surfaces and will also accept the sticking or attachment of non-stretchable tapes will add to their effectiveness, versatility and comfort many times so that in general it will allow a very valuable unit to be made for solving a major problem in the human being: "the wound bleeding." This will also be useful for preventing bleeding or oozing secretions after certain surgeries or wounds, etc. In such cases a combination of controllable pressure and dressing may prevent or diminish the swelling and disfiguration of the wound site and the area. The fact that the temperature of some units may be changed may be quite helpful as well. This can be done by fluid-filled balloons or even with the use of an electrically heated pad which can be incorporated in the support units as well. The clear units, balloons and bags will add a very important value to these units in providing an easy means of observation. The use of doors will be very useful in allowing direct inspection and treatment of the area. The use of second units for preventing and controlling bleeding during dressing, etc, can be of tremendous help in many war wounds. These will allow much easier work to be done in the wound when the bleeding can be stopped during the work. Incorporation of lights with switch and magnifiers may be very helpful in certain conditions and circumstances.

Disposable smaller or compact units for different areas of the body from fingers to limbs, etc., when using the same principles and purposes will be used in natural or man-made disasters which may save discomfort, time and lives. Even some models may be useful in controlling different hernias as Some Other Uses. The inventor believes that this idea has yet even more application than has been covered. He wishes to point some very troublesome circumstances in which bleeding is truly an ultra important problem that determines life or death in a very short time. Unfortunate cases such as a rupture of a tubal pregnancy, rupture of intra abdominal aortic aneurysem or similar conditions would kill a patient in a very short time unless the very expert team and needed operating room with all staff are ready to go. But where in the world would such ideal circumstances be available when needed? So for such circumstances the applicant introduces the use of a non-stretchable very large wrap that would be wrapped around the abdomen with combinations of many large balloons with many inflation ports that can be inflated simultaneously by hand or automatic means to provide/ heavy pressure to the abdomen of the patient and increase the intra-abdominal pressure to prevent bleeding until better help is available. The applicant does not argue with the fact that this is a very tough measure, and is very uncomfortable, and would have complications, but this is a true real life and death circumstance and the discomfort is worthwhile for a person who is to lose his/her only life in a matter of minutes. The treatment does not stop here: in gynecological cases, insertion of an inflatable balloon inside the uterus to expand and press the inner wall of the uterus and prevent bleeding; also in GI cases insertion of a balloon to the bleeding ulcer area (usually Gastro duodenal area is also suggested). This balloon will have the appropriate shape of the needed area. In other cases the balloon may have a shape of long tubular shape which has an empty center lumen that will allow passage of air, liquid, or other materials. This unit will be useful in conditions such as pressing the colon wall or nasal area, etc, so that the center area will not be occluded. Importantly, the outer surface of this balloon may allow pressure application on the gauze. This unit may be used easily to prevent bleeding or leakage of materials after conditions such as the removal of a polyp or similar condition. A similar approach may be considered in some other similar cases as well.

For bleeding from the nose a small soft balloon will be made by having an open tubing in its center. This balloon will have a proper shape to fit the inner space of the nostril and press to the mucous. This balloon will have a small tubing for inflation by a syringe or other means. This unit will also have an open tubing in its center to allow the motion of air for breathing to occur while the balloon is inflated. The outer surface of this balloon may be medicated with different medications such as antibiotics, anesthetics or lubricants, etc.

The benefits of such units and their uses is not to be limited only to human beings. It is intended to be made and used in animals of any species as well when applicable. In such cases similar units will be made to shape and match their body shape in needed areas.

We claim:

1. A device for applying pressure to a person's groin comprising a wrap holding a pressure-applying means against a person's groin, said wrap comprising a frontal portion overlying a person's groin for holding said pressure-applying means so that pressure of said pressure-applying means is exerted inwardly against a person's groin, said wrap further comprising an abdomen-wrap portion extending from said frontal portion for encircling the abdomen proximate the groin and a thigh-wrap portion extending from said frontal portion for encircling the thigh proximate the groin, wherein said frontal portion comprises a non-stretchable clear plastic to which both said abdomen- and thigh-wrap portions are attached, in which said non-stretchable clear plastic is a rigid clear plastic that straddles both the thigh-side and the abdomen side of a person's groin line and that has a size that fits in front of a person's body totally on one side of the vertical midline of the person's body.

2. A device as set forth in claim 1 in which said rigid clear plastic comprises a dome for providing clearance to one or more intravascular sheaths when the device is applied to a person.

3. A device as set forth in claim 1 in which said pressure-applying means comprises an inflatable balloon disposed beneath said rigid clear plastic, and said rigid clear plastic comprises a hole providing for said balloon to be placed in communication with an inflation means for inflating the balloon.

4. A device as set forth in claim 1 in which said abdomen-wrap portion includes a back support for supporting a portion of the back of a supine person that would otherwise be unsupported.

5. A device as set forth in claim 4 in which said back support separably mounts on said abdomen-wrap portion, comprising a tunnel through which said abdomen-wrap portion passes.

6. A device as set forth in claim 5 in which said back support comprises inflatable means for inflating the back support to a desired degree of support.

7. A device as set forth in claim 1 in which said pressure-applying means comprises a balloon and further including a rigid surface between said balloon and the person.

8. A device as set forth in claim 1 in which said rigid clear plastic comprises a door that opens and closes to allow direct access to an area that lies beneath the door when the door is closed.

9. A device as set forth in claim 1 in which said rigid clear plastic has a trapezoidal shape which comprises a longer of two parallel sides for overlying the abdomen and a shorter of said two parallel sides for overlying the thigh.

10. A device as set forth in claim 1 further including a rigid surface which is disposed beneath said rigid clear plastic and which is forced against the person by said pressure-applying means.

11. A device as set forth in claim 10 in which said rigid surface comprises a dome for providing clearance to one or more intravascular sheaths when the device is applied to a person.

12. A device as set forth in claim 1 further including a rigid surface which is disposed beneath said non-stretchable clear plastic and which is forced against the person by said pressure-applying means.

13. A device as set forth in claim 1 in which said abdomen-wrap and said thigh-wrap portions comprise respective separable attachments for adjusting the wrap to a person.

14. A device as set forth in claim 13 in which said separable attachments are disposed proximate an edge of said rigid clear plastic.

15. A device as set forth in claim 13 in which said non-stretchable clear plastic comprises four corners, said abdomen-wrap portion, when placed on a person, extending from a first upper corner to a second upper corner, and said thigh-wrap portion extending from a third lower corner to a fourth lower corner.

16. A device as set forth in claim 1 in which said pressure-applying means comprises a balloon disposed beneath said rigid clear plastic, and in which said balloon is clear and, when inflated to apply pressure to a person, has thickness that is smaller than its expanse, and further including a further rigid clear surface disposed between said balloon and the person.

* * * * *